United States Patent
Fechner et al.

(10) Patent No.: US 10,639,337 B2
(45) Date of Patent: May 5, 2020

(54) METHOD FOR TREATING CANCER WITH A COXSACKIEVIRUS B3 (CVB3) VARIANT

(71) Applicant: Technische Universität Berlin, Berlin (DE)

(72) Inventors: Henry Fechner, Berlin (DE); Ahmet Hazini, Berlin (DE); Vanessa Brueckner, Berlin (DE)

(73) Assignee: TECHNISCHE UNIVERSITÄT BERLIN, Berlin (DE)

( * ) Notice: Subject to any disclaimer, the term of this patent is extended or adjusted under 35 U.S.C. 154(b) by 64 days.

(21) Appl. No.: 15/720,850

(22) Filed: Sep. 29, 2017

(65) Prior Publication Data

US 2019/0099460 A1    Apr. 4, 2019

(51) Int. Cl.
| | |
|---|---|
| A61K 35/768 | (2015.01) |
| A61K 35/76 | (2015.01) |
| A61P 35/00 | (2006.01) |
| A61K 31/7105 | (2006.01) |
| C12N 7/00 | (2006.01) |

(52) U.S. Cl.
CPC ........ *A61K 35/768* (2013.01); *A61K 31/7105* (2013.01); *A61K 35/76* (2013.01); *A61P 35/00* (2018.01); *C12N 7/00* (2013.01); *C12N 2770/32321* (2013.01); *C12N 2770/32332* (2013.01); *C12N 2770/32371* (2013.01)

(58) Field of Classification Search
CPC ....................... C12N 15/86; C12N 7/00; C12N 2770/32321; C12N 2770/32332; C12N 2770/32371; A61K 31/727; A61K 38/162; A61K 39/12; A61K 35/768; A61K 35/76; A61K 31/7105; C07K 14/005; A61P 35/00
See application file for complete search history.

(56) References Cited

U.S. PATENT DOCUMENTS

2015/0037287 A1*  2/2015  Shafren ............... G01N 33/5011
                                                                   424/93.6

FOREIGN PATENT DOCUMENTS

CN         103981152 B  *  1/2015

OTHER PUBLICATIONS

Hazini A, Pryshliak M, Brückner V, Klingel K, Sauter M, Pinkert S, Kurreck J, Fechner H. Heparan Sulfate Binding Coxsackievirus B3 Strain PD: A Novel Avirulent Oncolytic Agent Against Human Colorectal Carcinoma. Hum Gene Ther. Nov. 2018;29(11):1301-1314. Epub Jun. 20, 2018.*
Miyamoto S, Inoue H, Nakamura T, Yamada M, Sakamoto C, Urata Y, Okazaki T, Marumoto T, Takahashi A, Takayama K, Nakanishi Y, et. al. Coxsackievirus B3 is an oncolytic virus with immunostimulatory properties that is active against lung adenocarcinoma. Cancer Res. May 15, 2012;72(10):2609-21. Epub Mar. 29, 2012.*
Zautner AE, Körner U, Henke A, Badorff C, Schmidtke M. Heparan sulfates and coxsackievirus-adenovirus receptor: each one mediates coxsackievirus B3 PD infection. J Virol. Sep. 2003;77(18):10071-7.*
Knelson EH, Nee JC, Blobe GC. Heparan sulfate signaling in cancer. Trends Biochem Sci 2014;39:277-288.*
Zautner AE, Korner U, Henke A, et al. Heparan sulfates and coxsackievirus-adenovirus receptor: each one mediates coxsackievirus B3 PD infection. J Virol 2003;77:10071-10077.*
Ranki T, Kanerva A, Ristimäki A, Hakkarainen T, Särkioja M, Kangasniemi L, Raki M, Laakkonen P, Goodison S, Hemminki A. A heparan sulfate-targeted conditionally replicative adenovirus, Ad5.pk7-Delta24, for the treatment of advanced breast cancer. Gene Ther. Jan. 2007;14(1):58-67. Epub Aug. 10, 2006.*
Ylä-Pelto J, Tripathi L, Susi P. Therapeutic Use of Native and Recombinant Enteroviruses. Viruses. Feb. 3, 2016;8(3):57.*
Schmidtke M, Braun H. Capsid protein, partial [Coxsackievirus B3]. GenBank: AIM18912.1. Dep. May 31, 2015.*
Schmidtke M, Zell R. Polyprotein capsid protein precursor, partial [Coxsackievirus B3]. GenBank: AAG23921.1. Dep. Jul. 14, 2016.*
Fechner H., et al. "Trans-complementation of vector replication versus coxsackieadenovirus-receptor overexpression to improve transgene expression in poorly permissive cancer cells." Gene Ther. 2000;7:1954-1968.
Stein EA., et al. "Combination of ma interference and virus receptor trap exerts additive antiviral activity in coxsackievirus b3-induced myocarditis in mice." J Infect Dis. 2015;211:613-622.
Pinkert S., et al. "Prevention of cardiac dysfunction in acute coxsackievirus b3 cardiomyopathy by inducible expression of a soluble coxsackievirus-adenovirus receptor." Circulation. 2009;120:2358-2366.
Andreoletti L., et al. "Viral causes of human myocarditis." Archives of cardiovascular diseases. 2009;102:559-568.
Andreoletti L., et al. "Active coxsackieviral b infection is associated with disruption of dystrophin in endomyocardial tissue of patients who died suddenly of acute myocardial infarction." J. Am. Col. I. Cardiol. 2007;502207-2214.
Ronellenfitsch S., et al. "First report of a Chinese strain of coxsackie b3 virus infection in a newborn in germany in 2011: A case report." Journal of medical case reports. 2014;8:164.
Schmidtke M., et al. "The viral genetic background determines the outcome of coxsackievirus B3 infection in outbred NMRI mice." J Med Virol 2007;79:1334-42.
Fukuhara H., et al. "Oncolytic virus therapy: A new era of cancer treatment at dawn" Cancer Sci, 107 (2016), 1373-1379.

(Continued)

*Primary Examiner* — Rachel B Gill
(74) *Attorney, Agent, or Firm* — Milstein Zhang & Wu LLC; Duan Wu, Esq.

(57) ABSTRACT

The present invention relates to a method for treating cancer in a subject in need thereof, comprising administering to said subject a therapeutically effective amount of a Coxsackie B3 group virus or a modified form thereof, wherein the cells of the cancer express a heparan sulfate (HS) receptor on their surface and the virus binds to said HS receptor, enters and accumulates in the cancer cells, whereby at least some cancer cells undergo viral lysis.

13 Claims, 10 Drawing Sheets
(5 of 10 Drawing Sheet(s) Filed in Color)
Specification includes a Sequence Listing.

(56) References Cited

OTHER PUBLICATIONS

Kaufman H., et al. "Oncolytic viruses: a new class of immunotherapy drugs" Nature Reviews Drug Discovery 14, 642-662 (2015).
Berry L., et al. "Potent Oncolytic Activity of Human Enteroviruses Against Human Prostate Cancer" The Prostate 68:577-587 (2008).
Shafren D., et al. "Systemic Therapy of Malignant Human Melanoma Tumors by a Common Cold-Producing Enterovirus, Coxsackievirus A21" Clinical Cancer Research, 10:53-60 (2004).
Skelding K., et al. "Systemic targeting of metastatic human breast tumor xenografts by Coxsackievirus A21." Breast Cancer Res Treat 113:21-30 (2009).
Miyamoto S., et al. "Coxsackievirus B3 Is an Oncolytic Virus with Immunostimulatory Properties That Is Active against Lung Adenocarcinoma" Cancer Res 72(10): 2609-2621 (2012).
Bergelson J., et al. "The Murine CAR Homolog Is a Receptor for Coxsackie B Viruses and Adenoviruses" J Med Virol 72(1): 415-419 (1998).
Bergelson J., et al. "Coxsackievirus B3 Adapted to Growth in RD Cells Binds to Decay-Accelerating Factor (CD55)" J Med Virol 69(3): 1903-1906 (1995).

\* cited by examiner

FIG. 2A

```
MGAQVSTQKTGAHETGLNASGNSIIHYTNIHYYKDAASNSANRQDPTQDPGKFTEPVKDI
MIKSLPALNSPTVEECGYSDRVRSITLGNSTITTQECANVVVGYGVWPDYLKDSEATAED
QPTQPDVATCRFYTLDSVQWQKTSPGWWWKLPDALSNLGLFGQNMQYHYLGRTGYTVKVQ
CNASKFHQGCLLVVCVPEAENGCATLDNTPSSAELLGGDSAKEFADKPVASGSNKLVQRV
VYNAGMGVGVGNLTIFPHQWINLRTNNSATIVMPYTNSVPMDNMFRHNNVTLMVIPFVPL
DYCPGSTTYVPITVTIAPMCAEYNGLRLAGHQGLPTMNTPGSCQFLTSDDFQSPSAMPQY
DVTPEMRIPGKVKNLMEIAEVDSVVPVQNVGEKVRSMEAYQIPVRSNECSGTQVPGFPLQ
PGYSSVFSRTLLGEILNYYTHWSGSIKLTFMFCGSAMATGKFLLAYSPFGAGAPTKRVDA
MLGTHVVWDVGLQSSCVLCIPWISQTHYRYVASDEYTAGGFITCWYQTNIVVPADAQSSC
YIMCFVSACNDFSVRLLKDTPFISQQNFYQGPVEDAITAAIGRVADTVGTGPTNSEAIPA
LTAAETGHTSQVVPGDTMQTRHVKNYHSRSESTIENFLCRSACVYFTKYANSGAKRYAEW
AITPRQAAQLRRKLEFPTYVRFDLELTFVITSTQQPSTTQNQDAQILTHQIMYVPPGGPV
PEKVDSYVWQTSTNPSVFWTEGNAPPRNSIPFLSIGNAYSNFYDGWSEFSRNGVYGINTL
NNMGTLYARHVNSGSTGPIKSTIRIYFKPKHVKAWIPRPPRLCQYEKAKNVNFQPSGVTT
TRQSITTMTN
```

FIG. 2B

```
                        SEQUENCE LISTING

<160> NUMBER OF SEQ ID NOS: 4

<210> SEQ ID NO 1
<211> LENGTH: 3294
<212> TYPE: DNA
<213> ORGANISM: Artificial Sequence
<220> FEATURE:
<223> OTHER INFORMATION: VP4-VP2-VP3-VP1

<400> SEQUENCE: 1
ttaaaacagc ctgtgggttg atcccaccca cagggcccat tgggcgctag cactctggta      60
tcacggtacc tttgtgcgcc tgttttatac cccctccccc aactgtaact tagaagcaac     120
acacaccgat caacagtcag cgtggcacac cagccacgtt ttgatcaagc acttctgtta     180
ccccggactg agtatcaata gactgctcac gcggttgaag gagaaagcgt tcgttatccg     240
gccaactatt tcgaaaaacc tagtaacacc gtggaagttg cagagtgttt cgctcagcac     300 tacccccagtg tagatcaggt cgatgagtca ccgcattccc cacgggcgac cgtggcggtg     360
gctgcgttgg cggcctgccc atggggaaac ccatgggacg ctctaataca gacatggtgc     420
gaagagtcta ttgagctagt tggtagtcct ccggcccctg aatgcggcta atcctaactg     480
cggagcacac accctcaagc cagagggcag tgtgtcgtaa cgggcaactc tgcagcggaa     540
ccgactactt tgggtgtccg tgtttcattt tattcctata ctggctgctt atggtgacaa     600
ttgagagatt gttaccatat agctattgga ttggccatcc ggtgaccaat agagctatta     660
tatatctctt tgttgggttt ataccactta gcttgaaaga ggttaaaaca ttacaattca     720
ttgttaagtt gaatacagca aaatgggagc tcaagtatca acgcaaaaga ctggggcaca     780
tgagaccggg ctgaatgcta gcggcaattc catcattcac tacacaaata ttaattatta     840
caaggatgcc gcatccaact cagccaatcg gcaggatttc actcaagacc cgggcaagtt     900
cacagaacca gtaaaagata tcatgattaa atcactacca gctctcaact cccccacagt     960
agaggagtgc ggatacagtg acaggtgag atcaatcaca ttaggtaact ccaccataac    1020
gactcaggaa tgcgccaacg tggtggtggg ctatggagta tggccagatt atctaaagga    1080
tagtgaggca acagcagagg accaaccgac ccaaccagac gttgccacat gtaggttcta    1140 taccccttgac tctgtgcaat ggcagaaaac ctcaccagga tggtggtgga agctgcccga    1200
tgctttgtcg aacttaggac tgtttgggca gaacatgcag taccactact taggccgaac    1260
tgggtatacc gtacatgtgc agtgcaatgc atctaagttc caccaaggat gcttgctagt    1320
agtgtgtgta ccggaagctg agatgggttg cgcaacgcta gacaacaccc catccagtgc    1380
agaattgctg gggggcgata gcgcaaaaga gtttgcggac aaaccggtcg catccgggtc    1440
caacaagttg gtacagaggg tggtgtataa tgcaggcatg ggggtgggtg ttggaaacct    1500
caccattttc ccccaccaat ggatcaacct acgcaccaat aatagtgcta caattgtgat    1560
gccatacacc aacagtgtac ctatggataa catgtttagg cataacaacg tcaccctaat    1620
ggttatccca tttgtaccgc tagattactg ccctgggtcc accacgtacg tcccaattac    1680
ggtcacgata gcccccaatgt gtgccgagta caatgggtta cgtttagcag ggcaccaggg    1740
cttaccaacc atgaatactc cggggagctg tcaatttctg acatcagacg acttccaatc    1800
gccatccgcc atgccgcaat atgacgtcac accagagatg aggatacctg gtgaggtgaa    1860
```

```
aaacttgatg gaaatagctg aggttgactc agttgtccca gtccaaaatg ttggagagaa  1920
ggtcaactct atggaagcat accagatacc tgtgagatcc aatgaaggat ctggaacgca  1980
agtattcggc tttccactgc aaccagggta ctcgagtgtt tttagtcgga cgctcctagg  2040
agagatcttg aactattata cacattggtc aggcagcata aagcttacgt ttatgttctg  2100
tggttcggcc atggctactg gaaaattcct tttggcatac tcaccaccag gtgctggagc  2160
tcctacaaaa agggttgatg ccatgcttgg tactcatgta gtttgggacg tggggctaca  2220
atcaagttgc gtgctgtgta taccctggat aagccaaaca cactaccggt atgttgcttc  2280
agatgagtat accgcagggg gttttattac gtgctggtat caaacaaaca tagtggtccc  2340
agcggatgcc caaagctcct gttacatcat gtgttttgtg tcagcatgca atgacttctc  2400
tgtcaggcta ttgaaggata ctcctttcat ttcgcagcaa aacttttacc agggcccagt  2460
ggaagacgcg ataacagccg ctatagggag agttgcggat accgtgggta cagggccaac  2520
caactcagaa gctataccag cactcactgc tgctgagaca ggtcacacgt cacaagtagt  2580
gccgggtgac accatgcaga cacgccacgt taagaactac cattcaaggt ccgagtcaac  2640
catagagaac ttcctatgta ggtcagcatg cgtgtacttt acgaagtatg caaactcagg  2700
tgccaagcgg tatgctgaat gggcaataac accacgacaa gcagcacaac ttaggagaaa  2760
gctagaattc tttacctacg tccggttcga cctggagctg acgtttgtca taacaagtac  2820
tcaacagccc tcaaccacac agaaccaaga cgcacagatc ctaacacacc aaattatgta  2880
tgtaccacca ggtggacctg taccagaaa agttgattca tacgtgtggc aaacatctac  2940
gaatcccagt gtgttttgga ccgagggaaa cgccccgccg cgcatgtcca taccgttttt  3000
gagcattggc aacgcctatt caaatttcta tgacggatgg tctgaatttt ccaggaacgg  3060
agtttacggc atcaacacgc taaacaacat gggcacgcta tatgcaagac atgtcaactc  3120
tggaagcacg ggtccaataa aaagcaccat tagaatctac ttcaaaccga agcatgtcaa  3180
agcgtggata cctagaccac ctagactctg ccaatacgag aaggcaaaga acgtgaactt  3240
ccaacccagc ggagttacca ctactaggca aagcatcact acaatgacaa atac         3294
```

<210> SEQ ID NO 2
<211> LENGTH: 850
<212> TYPE: PRT
<213> ORGANISM: Artificial Sequence
<220> FEATURE:
<223> OTHER INFORMATION: VP4-VP2-VP3-VP1

<400> SEQUENCE: 2

```
Met Gly Ala Gln Val Ser Thr Gln Lys Thr Gly Ala His Glu Thr Gly
1               5                   10                  15

Leu Asn Ala Ser Gly Asn Ser Ile Ile His Tyr Thr Asn Ile Asn Tyr
            20                  25                  30

Tyr Lys Asp Ala Ala Ser Asn Ser Ala Asn Arg Gln Asp Phe Thr Gln
        35                  40                  45

Asp Pro Gly Lys Phe Thr Glu Pro Val Lys Asp Ile Met Ile Lys Ser
    50                  55                  60

Leu Pro Ala Leu Asn Ser Pro Thr Val Glu Glu Cys Gly Tyr Ser Asp
65                  70                  75                  80

Arg Val Arg Ser Ile Thr Leu Gly Asn Ser Thr Ile Thr Thr Gln Glu
                85                  90                  95

Cys Ala Asn Val Val Val Gly Tyr Gly Val Trp Pro Asp Tyr Leu Lys
            100                 105                 110
```

```
Asp Ser Glu Ala Thr Ala Glu Asp Gln Pro Thr Gln Pro Asp Val Ala
            115                 120                 125

Thr Cys Arg Phe Tyr Thr Leu Asp Ser Val Gln Trp Gln Lys Thr Ser
        130                 135                 140

Pro Gly Trp Trp Trp Lys Leu Pro Asp Ala Leu Ser Asn Leu Gly Leu
145                 150                 155                 160

Phe Gly Gln Asn Met Gln Tyr His Tyr Leu Gly Arg Thr Gly Tyr Thr
                165                 170                 175

Val His Val Gln Cys Asn Ala Ser Lys Phe His Gln Gly Cys Leu Leu
            180                 185                 190

Val Val Cys Val Pro Glu Ala Glu Met Gly Cys Ala Thr Leu Asp Asn
        195                 200                 205

Thr Pro Ser Ser Ala Glu Leu Leu Gly Gly Asp Ser Ala Lys Glu Phe
    210                 215                 220

Ala Asp Lys Pro Val Ala Ser Gly Ser Asn Lys Leu Val Gln Arg Val
225                 230                 235                 240

Val Tyr Asn Ala Gly Met Gly Val Gly Val Gly Asn Leu Thr Ile Phe
                245                 250                 255

Pro His Gln Trp Ile Asn Leu Arg Thr Asn Asn Ser Ala Thr Ile Val
            260                 265                 270

Met Pro Tyr Thr Asn Ser Val Pro Met Asp Asn Met Phe Arg His Asn
        275                 280                 285

Asn Val Thr Leu Met Val Ile Pro Phe Val Pro Leu Asp Tyr Cys Pro
    290                 295                 300

Gly Ser Thr Thr Tyr Val Pro Ile Thr Val Thr Ile Ala Pro Met Cys
305                 310                 315                 320

Ala Glu Tyr Asn Gly Leu Arg Leu Ala Gly His Gln Gly Leu Pro Thr
                325                 330                 335

Met Asn Thr Pro Gly Ser Cys Gln Phe Leu Thr Ser Asp Asp Phe Gln
            340                 345                 350

Ser Pro Ser Ala Met Pro Gln Tyr Asp Val Thr Pro Glu Met Arg Ile
        355                 360                 365

Pro Gly Glu Val Lys Asn Leu Met Glu Ile Ala Glu Val Asp Ser Val
    370                 375                 380

Val Pro Val Gln Asn Val Gly Glu Lys Val Asn Ser Met Glu Ala Tyr
385                 390                 395                 400

Gln Ile Pro Val Arg Ser Asn Glu Gly Ser Gly Thr Gln Val Phe Gly
                405                 410                 415

Phe Pro Leu Gln Pro Gly Tyr Ser Ser Val Phe Ser Arg Thr Leu Leu
            420                 425                 430

Gly Glu Ile Leu Asn Tyr Tyr Thr His Trp Ser Gly Ser Ile Lys Leu
        435                 440                 445

Thr Phe Met Phe Cys Gly Ser Ala Met Ala Thr Gly Lys Phe Leu Leu
    450                 455                 460

Ala Tyr Ser Pro Pro Gly Ala Gly Ala Pro Thr Lys Arg Val Asp Ala
465                 470                 475                 480

Met Leu Gly Thr His Val Val Trp Asp Val Gly Leu Gln Ser Ser Cys
                485                 490                 495

Val Leu Cys Ile Pro Trp Ile Ser Gln Thr His Tyr Arg Tyr Val Ala
            500                 505                 510

Ser Asp Glu Tyr Thr Ala Gly Gly Phe Ile Thr Cys Trp Tyr Gln Thr
        515                 520                 525
```

```
Asn Ile Val Val Pro Ala Asp Ala Gln Ser Ser Cys Tyr Ile Met Cys
    530                 535                 540
Phe Val Ser Ala Cys Asn Asp Phe Ser Val Arg Leu Leu Lys Asp Thr
545                 550                 555                 560
Pro Phe Ile Ser Gln Gln Asn Phe Tyr Gln Gly Pro Val Glu Asp Ala
                565                 570                 575
Ile Thr Ala Ala Ile Gly Arg Val Ala Asp Thr Val Gly Thr Gly Pro
            580                 585                 590
Thr Asn Ser Glu Ala Ile Pro Ala Leu Thr Ala Ala Glu Thr Gly His
        595                 600                 605
Thr Ser Gln Val Val Pro Gly Asp Thr Met Gly Thr Arg His Val Lys
    610                 615                 620
Asn Tyr His Ser Arg Ser Glu Ser Thr Ile Glu Asn Phe Leu Cys Arg
625                 630                 635                 640
Ser Ala Cys Val Tyr Phe Thr Lys Tyr Ala Asn Ser Gly Ala Lys Arg
                645                 650                 655
Tyr Ala Glu Trp Ala Ile Thr Pro Arg Gln Ala Ala Gln Leu Arg Arg
            660                 665                 670
Lys Leu Glu Phe Phe Thr Tyr Val Arg Phe Asp Leu Glu Leu Thr Phe
        675                 680                 685
Val Ile Thr Ser Thr Gln Gln Pro Ser Thr Thr Gln Asn Gln Asp Ala
    690                 695                 700
Gln Ile Leu Thr His Gln Ile Met Tyr Val Pro Pro Gly Gly Pro Val
705                 710                 715                 720
Pro Glu Lys Val Asp Ser Tyr Val Trp Gln Thr Ser Thr Asn Pro Ser
                725                 730                 735
Val Phe Trp Thr Glu Gly Asn Ala Pro Pro Arg Met Ser Ile Pro Phe
            740                 745                 750
Leu Ser Ile Gly Asn Ala Tyr Ser Asn Phe Tyr Asp Gly Trp Ser Glu
        755                 760                 765
Phe Ser Arg Asn Gly Val Tyr Gly Ile Asn Thr Leu Asn Asn Met Gly
    770                 775                 780
Thr Leu Tyr Ala Arg His Val Asn Ser Gly Ser Thr Gly Pro Ile Lys
785                 790                 795                 800
Ser Thr Ile Arg Ile Tyr Phe Lys Pro Lys His Val Lys Ala Trp Ile
                805                 810                 815
Pro Arg Pro Pro Arg Leu Cys Gln Tyr Glu Lys Ala Lys Asn Val Asn
            820                 825                 830
Phe Gln Pro Ser Gly Val Thr Thr Arg Gln Ser Ile Thr Thr Met
        835                 840                 845
Thr Asn
    850

<210> SEQ ID NO 3
<211> LENGTH: 19
<212> TYPE: DNA
<213> ORGANISM: Unknown
<220> FEATURE:
<223> OTHER INFORMATION: Forward primer

<400> SEQUENCE: 3
ccctgaatgc ggctaatcc                                              19

<210> SEQ ID NO 4
<211> LENGTH: 20
<212> TYPE: DNA
```

```
<213> ORGANISM: Unknown
<220> FEATURE:
<223> OTHER INFORMATION: Reverse primer

<400> SEQUENCE: 4
attgtcacca taagcagcca                                              20
```

METHOD FOR TREATING CANCER WITH A COXSACKIEVIRUS B3 (CVB3) VARIANT

FIELD OF INVENTION

The invention relates to Coxsackievirus B3 group (CVB3) viruses and its derivatives for the use in medicine and particularly for treating subjects having cancer, which expresses a heparan sulphate surface receptor on the cancer cells.

BACKGROUND OF THE INVENTION

Virotherapy with oncolytic viruses (OV) is a new form of therapy for the treatment of malignant tumor diseases, which has demonstrated its effectiveness in several clinical trials in the last two decades (Fukuhara et al., 2016). The anti-tumor effect is based on a dual mechanism. One is the destruction of the tumor cells by the tumor cell-specific replication of the OV, wherein seemingly OVs do selectively replicate in cancer cells, spread within tumor tissue and lead to tumor destruction. On the other hand due to the viral replication immunological processes are induced, which leads to a systemic anti-tumoral immune response (Kaufman et al., review 2015). Various DNA viruses, such as adenovirus, parvovirus, vaccinia virus and herpesvirus, and RNA viruses, such as Coxsackie-A-virus (CVA), vesicular stomatitis virus and reoviruses have been used as OV for treatment of cancer.

RNA viruses have a short replication cycle and produce a very large number of progeny, which gives them an advantage relative to DNA viruses in oncolytic virotherapy. Moreover, RNA viruses may be safer, as they lack the potential for genotoxic effects caused by integration into the host genome. In the course of the last fifteen years, enteroviruses such as CVA21, echovirus 1 and poliovirus, which are single-stranded RNA-viruses and belong to the Picornaviridae family, were evaluated for their potential as oncolytic agents against melanoma, breast and prostate cancer (Berry et al., 2008; Shafren et al., 2004; Skelding et al., 2009). Poliovirus and Coxsackivirus of strains A and B from the genus Enterovirus (EV) of the family Picornaviridae have been considered as promising OV for the therapy of tumor diseases.

Recently, another member of this group, Coxsackievirus B3 group (CVB3), strain Nancy, was described as a novel OV for treatment of lung carcinomas. The most comprehensive studies concerning effectiveness so far have been conducted with the oncolytic poliovirus variant PVS-RIPO in glioblastomas and Coxsackievirus A21 (CVA21) in melanomas. Of the Coxsackie B viruses (CVB), only CVB3 Nancy as OV in lung carcinomas was comprehensively described in an in vivo mouse model (Miyamoto et al., 2012). There it was shown that wild-type CVB3 (Nancy) can lyse human lung carcinoma cell tumors in nude mice. At the same time, the authors showed that although CVB3 (Nancy) induced inflammatory side effects, they were not considered as severe and did not lead to the death of the animals. No treatment-related mortality, but moderate hepatic dysfunction and mild myocarditis were reported to be the main side effects of CVB3 Nancy treatment of lung carcinoma in mice.

A number of CVB3 strains have been characterized by their tissue tropism and organ toxicity in order to better understand virus-host interaction and pathogenesis caused by viral infection. Among these CVB3 strains, there are strains which are highly cardiotropic, such as CVB3 H3, 31-1-31, M2, HA or H310A1, whereas a number of other strains have been found to be low or non-cardiotropic, e.g. Nancy and PD. There are also CVB3 strains that preferentially infect the liver. Moreover, almost all known CVB3 strains are able to infect the pancreas.

The difference in pathogenicity is believed to be attributable to viral capsid proteins, which are directly involved in virus-cell attachment and virus uptake. In general, most of CVB3 strains utilize the Coxsackievirus and adenovirus receptor (CAR) as primary and the decay accelerating factor (DAF) as co-receptors to infect cells (Bergelson et al., 1998; Bergelson et al., 1995). However, recently it was found that the strain CVB3 PD has an additional and unique receptor tropism as it can use heparan sulfates (HS) to enter the cells (Zautner et al., 2003).

Furthermore, as it was previously shown that CVB3 Nancy induces severe inflammation of the pancreas and the heart in mice (Stein et al., 2015; Pinkert et al., 2009) and in addition, that some CVBs are associated with the development of inflammatory and dilated cardiomyopathies in humans (Andreoletti et al., 2009; Andreoletti et al., 2007) or that CVB3 (Nancy) has been described in connection with severe infections of children (Ronellenfitsch et al., 2014), it seemed questionable to what extent CVB3 Nancy could actually be considered a safe OV.

It is therefore an object of the present invention to overcome the described disadvantages of the state of the art OVs in the treatment of cancer, especially with respect to efficiency and safety of used OVs. Moreover, it is the aim of the present invention to provide a new variant of CVB3 with substantially improved oncolytic efficiency and safety compared to known strains such as e.g. CVB3 strain Nancy.

SUMMARY OF THE INVENTION

The present invention provides the following:

A method for treating cancer in a subject in need thereof, comprising administering to said subject a therapeutically effective amount of a Coxsackie B3 group (CVB3) virus or a modified form thereof, wherein the cells in the tumor and/or the cancer cells of the tumor express a heparan sulfate (HS) receptor on their surface, wherein the virus binds to said HS receptor, enters and accumulates in the HS expressing cells, and causes the infected cells to undergo viral lysis.

Further the method as above, wherein the CVB3 virus comprise at lease one or several alterations in amino acid sequence selected from the group comprising the amino acid residues K78, A80, A91, and 192 in the viral capsid protein 1 (VP1) and the amino acid residue M34 and Y237 in the viral capsid protein 3 (VP3).

Further the method as above, wherein the Coxsackie B3 group virus is selected from the group of CVB3 Nancy, 31-1-93, H3 and PD, all being characterized by at least one modification in the VP1 and/or VP3 surface protein.

Further the method as above, wherein the CVB3 virus is CVB3 PD-0 or a modified form thereof.

Further the method as above, wherein the range of viral dose is between about $5 \times 10^5$ to about $3 \times 10^8$ plaque forming units (PFU), preferably between about $3 \times 10^6$ to about $3 \times 10^7$ PFU and further preferred between about $3 \times 10^6$ to about $3 \times 10^8$ PFU Further the method as above, wherein the cancer is selected from the group of colorectal carcinoma, esophageal cancer, breast cancer, lung cancer, pancreatic cancer, prostate cancer, gastric cancer and liver cancer.

Further the method as above, wherein the HS receptor is a N- and/or a 6-O-sulfated heparan.

Further the method as above, wherein cells of the tumor substantially lacking or having expression of the Coxsackievirus and adenovirus receptor (CAR) and/or the decay-accelerating factor (DAF) on their surface.

A method for treating cancer in a subject in need thereof, comprising administering to said subject a therapeutically effective amount of a nucleic acid molecule or fragment thereof derived from a Coxsackie B3 group (CVB3) virus, wherein the cells in the tumor and/or the cancer cells of the tumor express a heparan sulfate (HS) receptor on their surface, wherein the nucleic acid molecule is transferred into the tumor and/or into the cancer cells, produces viral particles, which cause the transfected cells to undergo viral lysis, thereby releasing further virus particles which binds to HS receptor on cancer cells, enter these, accumulate in the HS expressing cells, and eventually causes lysis of the infected cells.

Further the method as above, wherein the CVB3 virus is a recombinant virus and comprises at least one additional nucleic acid molecule in its genomic sequence.

Further the method as above, wherein the at least one additional nucleic acid molecule is selected from the group of therapeutic, transgenic or small RNAs.

Further the method as above, wherein the CVB3 virus is selected from the group of CVB3 Nancy, 31-1-93, H3 and PD, which are all characterized by at lease one or several alterations in amino acid sequence selected from the group comprising the amino acid residues K78, A80, A91, and I92 in the viral capsid protein 1 (VP1).

Further the method as above, wherein the CVB3 virus is CVB3 PD or a modified form thereof.

Further the method as above, wherein the nucleic acid sequence of CVB3 PD comprise RNA residues giving rise to amino acid residues K78, A80, A91, and I92 in the viral capsid protein 1 (VP1).

Further the method as above, wherein the cancer is selected from the group of colorectal carcinoma, esophageal cancer, breast cancer, lung cancer, pancreatic cancer, prostate cancer, gastric cancer and liver cancer.

Further the method as above, wherein the HS receptor is N- and/or 6-0-sulfated.

Further a pharmacological composition for use in treating cancer in a subject in need thereof, comprising:
 a therapeutically effective amount of a Coxsackie B3 group (CVB3) virus or a modified form thereof as above, capable of lytically infecting said cancer; and
 at least one pharmaceutically acceptable excipient, diluent or carrier.

Further a pharmacological composition for use in treating cancer in a subject in need thereof, comprising:
 a therapeutically effective amount of a nucleic acid molecule derived from the CVB3 virus or a modified form as above, capable of lytically infecting said cancer; and
 at least one pharmaceutically acceptable excipient, diluent or carrier.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 2A. Nucleic acid sequence of the inventive CVB3 PD-0 (SEQ ID NO:1), including several differences in nucleotides towards the nucleotide sequence of state of the art CVB3-PD (GenBank ID: AF231765.1; ncbi.nlm.nih.gov/nuccore/AF231765) are indicated by small letters, bold and underlines, legend: Grey: 5UTR, Magenta: VP4, Blue: VP2, Red: VP3, Brown: VP1; In comparison to the CVB3-PD sequence in The Genbank (accession number: AF231765), the inventive CVB3 variant, PD-0 contains following nucleotide differences: C610T, A1801G, C1839T, C2248A, A2965G. The first letter indicates the nucleotide according to GenBank sequence, last letter indicates the nucleotide according to our sequence, number indicates the position of nucleotide.

FIG. 2B. Amino acid sequence of the inventive CVB3 PD-0 (SEQ ID NO:2), including several differences in amino acid residues towards the protein sequence of state of the art CVB3-PD (GenBank ID: AF231765.1; ncbi.nlm.nih.gov/nuccore/AF231765) are indicated by bold and underlines, legend: Magenta: VP4, Blue: VP2, Red: VP3, Brown: VP1.

FIGS. 3A and 3B. Expression level of surface CAR and DAF in colorectal carcinoma cell lines and HeLa cell line. Upper panel (FIG. 3A): Cell surface expression of CAR and DAF (dark gray graphs) was measured by flow cytometry using anti-CAR (RMCB) and anti-DAF (CD55) antibodies, respectively. As negative control (light gray graph), cells were stained only with the secondary antibody (Alexa Fluor® 488). HeLa cells were used as positive control due to high level expression of CAR and DAF. The black highlighted area represents the set gate. The percentages indicate the proportion of CAR or DAF positive cells. Lower panel (FIG. 3B): Diagram of cell surface expression of CAR and DAF in colorectal carcinoma cells. Columns shown means±SEM of three independent experiments.

FIG. 4. CVB3 strains have different oncolytic efficacy against colorectal carcinoma cells in vitro. The cell killing assay was performed with CVB3 Nancy, H3, PD-0 and 31-1-93 strains. HeLa cells and DLD1, Colo680H, Colo205, Colo320, and LS174T colorectal carcinoma cells were infected with either 1, 10 or 100 MOI of virus. Cell viability was determined 24 h, 48 h and 72 h post infection by crystal violet staining.

FIGS. 5A-5C. In vivo oncolytic efficiency of inventive CVB3 strains in DLD1 xenograft mouse model. DLD1 cells were subcutaneously inoculated into the right and left flank of BALB/c nude mice. One of the inoculated tumor was intratumorally injected with single dose ($3\times10^6$ PFU) of the CVB3 strains (FIG. 5A) 31-1-93 (n=6), (FIG. 5B) Nancy (n=6) and (FIG. 5C) PD-0 (n=5), respectively, at 6 days after tumor inoculation. Control group (n=4) was not treated. Tumor volumes are shown as means±SEM. CVB3 31-1-93 infected mice died 6 days after viral injection. CVB3 Nancy infected mice were sacrificed at day 8 after viral injection, at which time they were moribund, CVB3 PD-0 and un-injected control mice were sacrificed at day 10 after viral injection. *, $P<0.05$; , $P<0.01$; *, $P<0.001$ compared to the control.

FIGS. 6A and 6B. Infectivity and replication activity of CVB3 Nancy and PD-0 strain in harvested tumors. (FIG. 6A) Left: virus titers in CVB3 Nancy and PD injected tumors. Right: virus titers in the un-injected tumor, * $P<0.05$; n.s. not significant; (FIG. 6B) Presence and localization of CVB3-Nancy and PD-0 RNA treated and untreated tumors were determined by in situ hybridization using DIG-labeled RNA hybridization probes. Magnification, 100-fold.

FIG. 7. Kaplan-Meier survival curves for the mice. Animals died or were sacrificed as described under FIG. 5. The control group mice were sacrificed when the tumor burden reached an upper limit of 500 mm³ for reasons of animal welfare. P=0.0006.

(FIG. 8A) Amount of replicating virus. Plaque assays for the detection of replicating virus was performed for the heart, liver, spleen, brain and kidney, whereas the amount of virus in the pancreas was determined by quantitative RT-PCR. Note: Because of almost complete tissue destruction, pancreas could be harvested from only four of six animals of the CVB3 Nancy treated group for viral genome detection. (FIG. 8B) Histological examination of mouse tissues. Organ sections were stained with hematoxylin and eosin (magnification of images 200-fold). All Nancy infected animals showed complete destruction of the exocrine pancreas (stars represent areas of tissue destruction). Inflammation within the myocardium (arrows) was detected in all Nancy infected animals. All PD-0 infected animals were free of pathological alterations in all investigated organs. Mock represent untreated tumor bearing animals. No alteration of tissues was seen in these animals. Shown are representatives of each group.

DETAILED DESCRIPTION OF THE INVENTION

Figure 1:
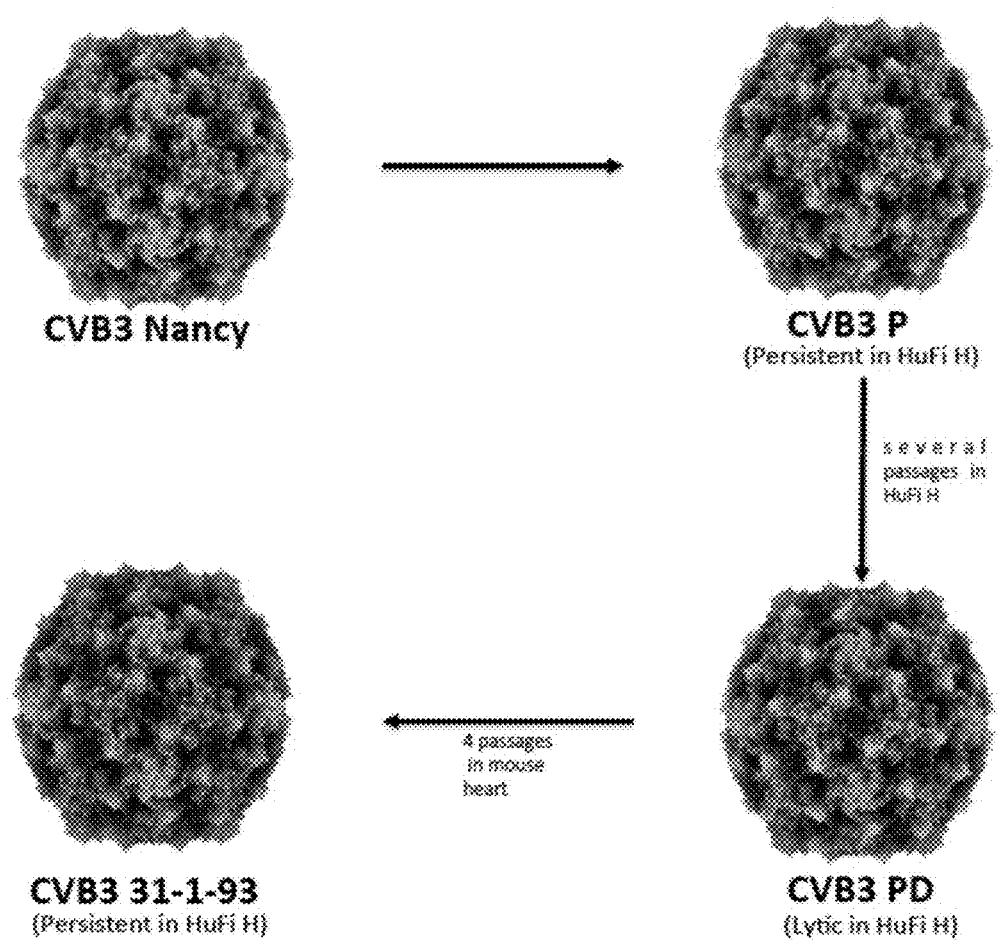
FIG. 1. Model for the successful generation of the inventive CVB3 PD by serial passaging.

To improve the host range and utilize the unique receptor tropism, a novel CVB3 PD variant was generated from the pre-described CVB3 PD by passaging. For this, the pre-described CVB3 variants were treated by serial passaging in specific target cells in vitro and in tissues in vivo (FIG. 1). Thus, a modified CVB3 variant PD—which is in the following and in the examples regularly addressed as PD-0— could be isolated after 13-fold passaging of the CVB3 variant CVB3 P in human fetal primary fibroblast cells H (HuFi H). In contrast to the CVB3 P variant, which induces a persistent CVB3 infection in HuFi H, PD-0 was able to completely lyse HuFi H cell cultures (FIG. 1).

It has been shown that in the newly generated CVB3 PD-0 variant, four amino acid (AA) substitutions were detected in the N-terminal area of the VP1 domain. It is believed that due to at least one or two of these mutations, PD-0 can use heparan sulfates at the cell surface in addition to the CVB3 receptors CAR and DAF for incorporation into the cell. This is particularly important as the CAR is known to be the primary CVB3 receptor responsible for the infection of tumor cells and which expression is regarded to be low on some tumor cells (Fechner et al., 2000).

Accordingly, the selection of the new CVB3 variant and the identification of sequence alterations, which lead to the use of alternative receptors and, thus, alternative host ranges, provides substantial improvements in the inventive method of treating cancer, wherein the cancer comprises cells expressing heparin sulfates on its cell surface.

According to one embodiment of the invention, the CVB3 PD-0 or modified form thereof shows at least one mutation distinct from the previously described CVB3 PD variants. It is believed—without being bound by the theory—that an exchange of at least one or more amino acid residues selected from the group consisting of amino acid residue K78, A80, A91, and 192 in the viral capsid protein 1 (VP1) and/or the amino acid residue M34 and Y237 in the viral capsid protein 3 (VP3) are responsible for the advantageous host range variations and the capacity of infecting HS expressing tumor cells. Accordingly, it has been shown that the inventive CVB3 PD strains (CVB3 PD-0) comprising one or several of these VP1 modifications and/or one or both of these VP3 modifications are capable of using HS and also subtypes of HS on target cell surface to mediate entry of the inventive CVB3 PD variant into target cells.

It had been previously shown that CVB3 Nancy induces severe inflammation of the pancreas and the heart in mice (Stein et al., 2015; Pinkert et al. 2009). In addition, CVBs are associated with the development of inflammatory and dilated cardiomyopathies in humans (Andreoletti et al., 2009; Andreoletti et al., 2007) and CVB3 Nancy has been described in connection with severe infections of children (Ronellenfitsch et al., 2014). Consequently, it seemed questionable to us to what extent CVB3 Nancy could actually be considered a safe OV.

It is therefore an object of the present invention to overcome at least partially the described disadvantages of the state of the art OVs in the treatment of cancer, especially with respect to efficiency and safety of used OVs. Moreover, it is the aim of the present invention to compare the oncolytic efficiency and safety of the CVB3 strains Nancy, H3, 31-1-93 and PD in treating human colorectal cancer as an exemplary candidate cancer type to be treated by CVB3 OVs.

This object has been solved by a method for treating cancer in a subject in need thereof, comprising administering to said subject a therapeutically effective amount of a modified Coxsackie B3 group (CVB3) virus according to claim 1.

Moreover, the present application also provides a method for treating cancer in a subject in need thereof, comprising administering to said subject a therapeutically effective amount of a nucleic acid molecule derived from the newly characterized Coxsackie B3 group (CVB3) variant or a modified form thereof. Eventually, also provided is a pharmacological composition for use in treating cancer in a subject in need thereof, comprising: i) a therapeutically effective amount of the modified Coxsackie B3 group (CVB3) virus thereof capable of lytically infecting said cancer and ii) at least one pharmaceutically acceptable excipient, diluent or carrier; as well as a pharmacological composition for use in treating cancer in a subject in need thereof, comprising: i) a therapeutically effective amount of a nucleic acid molecule derived from the modified Coxsackie B3 group (CVB3) virus, capable of lytically infecting said cancer ii) and at least one pharmaceutically acceptable excipient, diluent or carrier.

Thus, the invention provides a novel method for treating cancer in a subject in need thereof, where the cancer can be characterized by comprising heparin sulfate expressing cells (either cancer cells or neighboring cells) and where the method comprises administering to said subject a therapeutically effective amount of a Coxsackie B3 group (CVB3) virus or a modified form thereof, which infects the cells of the cancer and/or in the cancer expressing a heparan sulfate (HS) receptor on their surface by binding of the virus binds to said HS receptor, entering and eventually lysing the infected cells, whereby at least some of the infected cells are cancer cells, which undergo viral lysis.

In an embodiment of the present invention, the Coxsackie B3 group virus is selected from the group of CVB3 Nancy, 31-1-93, H3 and PD, which have been modified by introducing at least one or several of the AA modifications in the VP1 and/or VP3 surface protein, which have been identified to be involved or responsible for the binding to the heparin sulfate receptor. The amino acid modifications may be due to a base pair exchange on the nucleic acid sequence and will lead to an alteration or exchange of at least one or more amino acid residues selected from the group consisting of amino acid residue K78, A80, A91, and 192 in the viral capsid protein 1 (VP1) and/or at least one or both of the amino acid residue M34 and Y237 in the viral capsid protein 3 (VP3) of CVB3.

According to a preferred embodiment the Coxsackie B3 group virus is CVB3 PD-0 or a modified form thereof. CVB PD-0 comprises an exchange of at least one or more amino acid residues selected from the group consisting of amino acid residue K78, A80, A91, and 192 in the viral capsid protein 1 (VP1) and/or and at least one or both of the amino acid residue M34 and Y237 in the viral capsid protein 3 (VP3).

A "subject in need" may be any mammal in need of treatment according to the invention. The subject may be a human or an individual of any species of social, economic or research importance including, but not limited to, mice, rats, dogs, cats, sheep, goats, cows, horses, pigs, non-human primates, and humans. In a preferred embodiment, the subject in need is a human.

In the methods of the present invention by the term "viral lysis" is meant, that a sufficient number of cells (at least one) lyse as a consequence of direct infection with at least one virus particle (direct viral lysis). Moreover, events leading to lysis of cancer cells without a former infection of this at least one cancer cell by an at least one virus particle, but caused or triggered by effects caused by the presence of virus-infected neighboring cells—such cells possibly also being immune cells or other cell types being present in a tumor but not being cancer cells themselves (indirect viral lysis) are also included by that definition. The same is true also for e.g., a systemic anti-tumoral immune response caused by immunological processes induced by e.g. increased viral replication. A combination of direct lysis and indirect viral lysis events is particularly advantageous and included by this definition.

The "Coxsackie B3 group virus" according to the present invention may be any Coxsackie B3 group virus including known and classified Coxsackie B3 group viruses and yet to be classified Coxsackie B3 group viruses. The Coxsackie B3 group virus may be selected from the group consisting of both prototype and clinically isolated viruses. It may be naturally occurring or as claimed a "modified form thereof". The Coxsackie B3 group virus is "naturally-occurring" when it can be isolated from a source in nature and has not been intentionally modified in the laboratory—for instance the Coxsackie B3 group virus my be obtained from a human patient.

According to another embodiment of the invention, the range of viral dose is between about $5\times10^5$ to about $1\times10^8$ plaque forming units (PFU), preferably between about $1\times10^6$ to about $1\times10^7$ PFU and most preferred between about $3\times10^6$ to about $1\times10^7$ PFU. It is also provided that the application of the viral dose is administered 2-, 3-, or 4-times depending of the size of the tumor, the patients response, the tumor regression rate and also the body weight of the patient. Typically, a dose of about $4.5\times10^6$ PFU/kg for a 70-kg patient is to be considered.

In methods according to the present invention, a Coxsackie B3 group virus or a modified form thereof or a nucleic acid molecule derived from a Coxsackie B3 group virus or a modified form thereof and combinations of the said may be administered either in a single dose, or in multiple doses. The multiple doses may be administered concurrently, or consecutively (e.g., over a period of days or weeks). Typically, in therapeutic applications the treatment would be for the duration of the disease condition, e.g. at least until the respective cancer is no longer detectable by conventional means. Typical treatment regimes are known in the state of the art.

The mode of administering of the inventive, Coxsackie B group virus or a modified form thereof or a nucleic acid derived from the Coxsackie B3 group virus or a modified form thereof as well as combinations of the said to said subject in need thereof may be orally, intratumorally, intravenously, intraperitoneally and/or intramuscularly.

Surprisingly, the inventors have found that intratumoral injection of tumor bearing mice with any of the used virus strains led to significant inhibition of growth of the injected tumor. Even more surprisingly, a similar growth suppression was also observed for the distant, non-injected subcutaneous tumor. Whereas, these results demonstrate per se the efficacy of CVB3-mediated oncovirotherapy in a cancer type, which comprises cancer cells or other cells expressing and exposing heparin sulfate on the cell surface. According to one embodiment the method of the invention showed to be particularly effective in treating colorectal cancer. Particularly advantageous seems to be the growth suppression of the untreated tumor, which reveals the very promising potential of the CVB3-strains according to the present invention for not only treating the primary tumor but also for treating metastatic or disseminated cancer.

Surprisingly, the inventor could detect CVB3-PD-0 genomes in immune cells and their identified specific localization within the tumor mass or on the border between the tumor stroma and tumor cells (FIG. 6B) suggests that virus-induced immune-mediated mechanisms may be involved in anti-tumor efficiency. Moreover, these findings may interestingly indicate—without being bound by that theory—that immune cells may be infected by the inventive virus strains and be or become carriers and probably a reservoir for hematogenous distribution of the therapeutic viruses within a tumor but also to distant tumors.

As mentioned above, the way of administering the CVB3 PD virus of the invention is according to one embodiment an oral administration. This way of administering a therapeutic OV is particularly interesting for Coxackievirus in general but even more for the virus according the invention which has a strong host range tropism and preferably infects cells with an heparan sulfate receptor on the cell surface. Such heparan sulfate receptor expressing cells—preferably immune cells—can, thus, be used as carriers suitable to transporting the oncolytic CVB3 from a port of entry location e.g. in the Peyer's patches or the tonsils to the actual side of a tumor to be treated.

Most importantly, treatment with the inventive CVB3 PD virus or modified form thereof according to the present invention,—which are referred to in the following often with PD-0—did not show any virus-induced side effects, especially no systemic infection. E.g., the inventors could show that virus could not be recovered from the organs of animals treated with the CVB3 PD virus or modified form. Therefore, herein disclosed findings reveal that the inventive PD-0 and variants thereof are an efficient and safe CVB3 strain for treatment of cancer cells according to the present invention. As CVB3 PD utilizes a heparin sulfate receptor, but Nancy and 31-1-93 need CAR and DAF to infect cells, the specific receptor tropism of the inventive CVB3 PD-0 is considered to be a important feature for the claimed method of treatment and its safety advantages, namely to prevent from any infection of normal tissues in vivo.

In the methods according to the present invention, the CVB3-PD-0 virus or a modified form thereof or a nucleic acid molecule derived from said virus or a modified form thereof and combinations of the said may be administered in combination with one or more adjuvants or agents capable of modulating or suppressing an immune response in the subject to be treated. Thereby, preferably it may allow a more efficacious viral infection and/or viral lytic and/or therapeutic outcome. Typically capable agents are well known by a person skilled in the art.

In methods according to the present invention, the CVB3 virus or a modified form thereof or a nucleic acid molecule derived from the CVB3 group virus or a modified form thereof and combinations of the said will be co-administered with a therapeutically effective amount of at least one secondary anticancer agent. Typically capable anticancer agents are well known by a person skilled in the art. In an embodiment of the invention the at least one secondary anticancer agent is a chemotherapeutic agent. Typically chemotherapeutic agents are well known by a person skilled in the art.

Also, in methods according to the present invention the CVB3 virus or a modified form thereof or a nucleic acid molecule derived from the CVB3 virus or a modified form thereof and combinations of the said will be used in combination with radiotherapy. Alternatively, radiotherapy can be combined with said at least one secondary anticancer agent.

Moreover, the methods according to the present invention can be used in combination with therapeutic regimes and modalities well known by an artisan.

Interestingly, recent findings have shown that one or several of these four amino acid residues in VP1 are sufficient to allow infection and also induce "lytic" infections in both DAF- and CAR-negative cell lines—without being bound by this theory—suggesting that said at least one or several of these four modified residues in VP1 are the molecular basis of extended cell tropism of the inventive CVB3 PD variant and are involved in target cell receptor binding and entry into the target cell of CVB3 PD.

According to a further embodiment of the invention, the cancer to be treated is selected from a cancer that has been identified as comprising cancer cells, which express heparan sulfate on the surface of the cancer cells. The exposure of heparan sulfates on the surface of cancer cells can be tested with commercially available heparan sulfate antibodies in e.g. flow cytometric methods, western bolts or Elisa assays. Heparan sulfate specific antibodies or Elisa kits are available from, e.g., LSBio Inc., Seattle, Wash., USA.

According to further embodiments, the cancer to be treated is selected from the group of colorectal carcinoma, esophageal cancer, breast cancer, lung cancer, pancreatic cancer, prostate cancer, gastric cancer and liver cancer. According to an embodiment the cancer is colorectal carcinoma.

According to another embodiment of the invention, the HS receptor is N- and/or 6-O-sulfated. Interestingly, it was found that these specific heparan receptor modifications, i.e. N- or 6-O-sulfated heparan receptors at the surface of cancer cells can also mediate internalization of the inventive CVB3 PD variant.

It has been pre-described that there are three 6-O-sulfotransferases (60ST1-3) and seven 3-O-sulfotransferases triggering the 6-O- and 3-O-Sulfation of heparans in vertebrates. Accordingly, cancer comprising cancer cells with HS on the surface, which can be treated according to the present invention, can also be detected or identified, e.g. after a cancer biopsy by the detection of the corresponding sulfotransferases or even by the detection of the RNA of such sulfotransferases in cancer cells.

Accordingly, the expression of heparan sulfate D-glucosaminyl 6-O-sulftransferase-2 (HS6ST2) enzyme, which is necessary for the synthesis of N- and/or 6-O-sulfated heparan receptors is one good marker for the suitability of cancer cells that can be treated effectively with the described method and the described CVB3 variants.

Additionally, HS6ST2 mRNA expression was hardly or not at all found being expressed in respective non-cancerous cell tissues. This may be a promising finding as this would argue for an increased safety of the use of CVB3 viruses or modified forms thereof according to the present invention. This, because of the use of N- and 6-O-sulfated heparan receptors at a cell surface for infection of that cell by a virus according to the present invention, wherein the expression of N- and 6-O-sulfated heparan surface receptors is (essentially) restricted—without being bound by that theory—to the surface of cancer cells. This in turn hinders uncontrolled infection of non-cancerous tissue, lacking the expression of said heparan receptors, thereby increasing the safety of said virus and said nucleic acid, derived from said virus for medical usage.

Also for the specific heparin sulfate receptor, namely N- and 6-O-sulfated heparan, which can be found at a cell surface of cancer cells suitable for treatment according the present invention anti N- and 6-O-sulfated heparan receptor antibodies are well known and commercially available e.g. by LSBio Inc., Seattle, Wash., USA. Western blots or ELISAs using these antibodies may be a proper mean to prove expression of N- and 6-O-sulfated heparan receptor expression in cancer cells relative to control samples, i.e. respective non-cancerous tissue samples, e.g. colorectal cancer cells relative to non-cancerous colorectal tissue sample. Also, antibodies detecting the presence of anti-Heparan Sulfate 6-O-Sulfotransferase 3 (HS6ST3), the enzyme, which is necessary for the synthesis of N- and 6-O-sulfated heparan receptors may be used as expression indicator for 6-sulfated heparan receptors.

This is especially of interest if cells of a target cancer will substantially lack expression of the CAR and/or the DAF on their surface. The more as certain CVB3 variants, which are dependent on CAR and/or DAF to enter the cells, cannot enter cells if these cells essentially lacking expression of one or both of said receptors. However—without being bound by that theory—the inventive CVB3 PD variants and modified forms thereof, which only need expression of certain heparan sulfated receptors for infection would be capable to infect cancerous cells expressing these heparan sulfated receptors.

Therefore, according to an embodiment of the invention the treatment is particularly suitable for cells of a cancer, wherein the cancer cells substantially lacking expression and/or exposure of the Coxsackievirus and adenovirus receptor (CAR) or the decay-accelerating factor (DAF) on their surface.

In methods according to the present invention, the term "substantially lacking expression" refers to a protein expression on cell surface in which all or substantially all cells, e.g. more than 70%, more than 75%, more than 80%, more than 85%, more than 90%, more than 95%, more than 98%, more than 99%, or 100% of a cancer of a certain tissue origin do not express said respective proteins on their surface compared to the surface expression level of the respective normal (non-cancerous) tissue of origin as measured by flow cytometry using commercially available antibodies, precisely commercially available anti-DAF- or anti-CAR-antibodies, e.g. those as used herein.

According to another embodiment of the invention, the cells of the cancer show some expression of the CAR or the DAF on their surface.

Moreover, a method for treating cancer in a subject in need thereof is provided, which comprises administering to said subject a therapeutically effective amount of a nucleic acid molecule derived from a Coxsackie B3 group virus or a modified form thereof, wherein the cells of the cancer express a heparan sulfate (HS) receptor on their surface and said nucleic acid encodes for a virus, which binds to said HS receptor, enters and accumulates in the cancer cells, whereby at least some cancer cells undergo viral lysis.

In the context of the present invention, under the term "therapeutically effective amount" is meant, that a Coxsackie B3 group virus or a modified form thereof respectively a nucleic acid derived from a Coxsackie B3 group virus or a modified form thereof or combinations of said virus and said nucleic acid is administered in an amount that is sufficient to treat the respective cancer.

A cancer according to the inventions of the present invention is "treated", if administration of the said virus or the said nucleic acid to cells of the respective cancer effects viral lysis of at least some of the cancer cells, resulting in at least a reduction of tumor burden, tumor growth or tumor cell viability and/or preferably in an increase of the life span of a treated subject in need thereof. The effective amount will be determined on an individual basis and may be based at least in part, on consideration of the CVB3 virus or modified form thereof, the body weight, age, gender of the subject to be treated (subject in need thereof) and the type, extent and other characteristics of the respective cancer to be treated.

In methods of the invention, the CVB3 virus or modified form thereof or nucleic acid molecule derived from the Coxsackie B3 group virus or a modified form thereof may be administered to a respective cancer in the individual subject in need thereof. A combination of different serotypes and/or different strains and/or different species and/or different genera of CVB3 virus, such as CVB3 virus from different species of animal, may be used. If desired, the Coxsackie B group virus can be chemically or biochemically pretreated, e.g., by treatment with a protease, such as chymotrypsin or trypsin prior to administration to the neoplasm. Such pretreatment will lead to removal of the outer coat of the virus and may thus result in improved infectivity of the virus. Combinations of at least two different CVB3 viruses and/or modified forms thereof as well as combinations of at least two different nucleic acids derived from the CVB3 virus and/or modified forms thereof may be administered. Also, combinations of the said at least two different CVB3 viruses and/or modified forms thereof together with at least one nucleic acid derived from the CVB3 virus and modified form thereof may be administered. And, combinations of the said at least two different nucleic acids derived from the CVB3 virus and/or modified form thereof together with at least one CVB3 virus and/or modified forms thereof may be administered. The CVB3 virus or modified form thereof may be administered or applied in combination with other additional viruses. E.g., the applied CVB3 virus or modified form thereof will be administered with at least one strain or serotype or species or genera of Coxsackie B virus or modified forms thereof, which have either the same receptor requirements for cell infection as the CVB3 virus or modified form thereof of the invention, i.e. the HS receptor tropism or different receptor requirements.

According to an embodiment of the invention, the CVB3 virus genome sequence comprises at least one or several modified nucleic acid molecule.

In the sense of the present invention, a "nucleic acid molecule derived from a Coxsackie B3 group (CVB3) virus or a modified form thereof" may be understood as to include any viral nucleic acid, e.g. viral vectors, the complete viral RNA genome or a sufficient part thereof including complementary DNA (cDNA) versions of the said to permit generation of a lytic response in virus-infected cancer cells or generation of new viral particles, which then will cause a lytic response in the cell and be release ready for the infection of further—sometimes—neighboring cells.

In a further embodiment of the method of the invention, the viral nucleic acid sequence can be used as vector or can incorporate additional transgenic or therapeutic nucleic acid molecules, which are selected from the group of therapeutic transgenes or small RNAs. Therapeutic transgenes, may comprise a RNA transcript of therapeutically interesting cDNAs or other small RNAs, e.g. microRNA, siRNAs (e.g. microRNA-target sites (miR-TS)), which are well known by an artisan.

As a result of the incorporation of transgenic or therapeutic nucleic acid molecules into the genome or nucleic acid sequence of the CVB3 virus, the present invention also provides recombinant Coxsackie B3 group (rCVB3) viruses.

According to another embodiment of the invention, the CVB3 PD or a modified form thereof comprise nucleic acid sequence modifications giving rise to at least one or several modified amino acid residues selected from the group of amino acid residues K78, A80, A91, and 192 in the viral capsid protein 1 (VP1) and/or at least one or both of the amino acid residue M34 and Y237 in the viral capsid protein 3 (VP3).

According to one interesting embodiment of the invention, the treatment method even works, where cancer cells in the cancer to be treated do substantially lack a HS expression or exposure on the cell surface and at the same time in this tumor are neighboring cells (immune cells or other cell types, which do express HS on their surface. In this case the CVB3 virus of the invention will be infecting the neighboring cells (so called bystander cells) and will in a first step lyse such cells, subsequently and due to the amount of virus present in the cancer or at the location of the tumor, also the cancer cells will become infected and lysed. Accordingly, the present invention also provides in one embodiment a therapy for the treatment of a tumor, which does not comprise cancer cells expressing HS on the surface, but which (as shown in a biopsy) is infiltrated by other cells which do express HS on their surface and which therefore provide after the infection with the virus of the invention intratumoral virus production centers. In this case it is helpful but not necessary if the cancer cells would be capable of expressing and presenting on their cell surface the Coxsackievirus and adenovirus receptor (CAR) and/or the decay-accelerating factor (DAF) on their surface. Accordingly, in one embodiment of the invention the cells of the cancer show expression of the CAR or the DAF on their surface.

Beside the above-described therapeutic approach, the method of the present invention also provides the treatment of a target cancer, which is substantially lacking expression of the CAR and/or the DAF on their surface. This is particularly the case, because CVB3 PD-0, which only needs expression of heparan sulfated receptors for infection—without being bound by that theory—is capable to infect such cancer cells expressing these heparan sulfated receptors.

This is particularly advantageous as other CVB variants, which are dependent on CAR and/or DAF to enter the cells, cannot enter such cancer cells lacking expression of one or both of said receptors.

According to one further embodiment of the method of the present invention, the HS receptor is a N- and/or a 6-O-sulfated heparan.

According to another aspect, the present invention relates to a pharmacological composition for use in treating cancer in a subject in need thereof, comprising: i) a therapeutically effective amount of the Coxsackie B3 group (CVB3) virus, as herein described or a modified form thereof, capable of lytically infecting said cancer and ii) at least one pharmaceutically acceptable excipient, diluent or carrier.

According to still another embodiment, the inventive pharmacological composition for use in treating cancer in a subject in need thereof, comprises: i) a therapeutically effective amount of a nucleic acid molecule derived from the CVB3 virus or a modified form thereof as herein described, capable of lytically infecting said cancer and ii) at least one pharmaceutically acceptable excipient, diluent or carrier.

Suitable pharmaceutically acceptable excipient, diluent and carriers according to the inventive pharmacological composition are well known by an artisan. In brief, examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from 10% to 99.9% by weight of the pharmacological compositions.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colouring agents. When used in capsule form the capsules may be coated with compounds such as glyceryl monostearate or glyceryl distearate, which delay disintegration.

The pharmacological composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

EXAMPLES

In the following the invention will be described in more detail by reference to specific examples, which should not be construed as in any way limiting the scope of the present invention.

Cell Lines

HeLa cells were cultured in Dulbecco's modified Eagle's medium (DMEM) (Gibco BRL, Karlsruhe, Germany) supplemented with 5% fetal calf serum (FCS) and 1% penicillin-streptomycin. Colorectal carcinoma cell lines (DLD1, Colo205, Colo680h, Colo320) were grown in RPMI 1640 supplemented with 10% FCS, 1% penicillin-streptomycin, 1% L-Glutamine and 1 mM Na-Pyruvate (Invitrogen, Karlsruhe, Germany). LS174T cells were maintained in EMEM (Lonza, Basel, CH) and supplemented with 10% FCS, 1% penicillin-streptomycin, 1% L-Glutamine and 1 mM Na-Pyruvate (Invitrogen, Karlsruhe, Germany).

Viruses

The inventive CVB3 strain PD was derived by serial passages of the CVB3 strain P on HuFi cells (26). The cardiotropic CVB3 strain 31-1-93 was isolated from heart tissue after four heart passages of PD in outbred NMRI mice. CVB3 PD and 31-1-93 were propagated in CAR/DAF-negative CHO-K1 and in HeLa cells, respectively, before use. CVB3 strain Nancy (ATCC VR30) was propagated in HeLa cells. CVB3 H3 was generated by transfection of the cDNA containing plasmid pBK-CMV-H3 into HEK293T cells using Polyethylenimine Max (Polyciences, Warrington, Pa., USA). Completely lysed cells were harvested 48 h post transfection and the virus was stored in aliquots after three freeze/thaw cycles and removal of the cell debris by centrifugation.

Viral Plaque Assay

Viral plaque assays were carried out as previously described (Fechner et al., 2008). Briefly, HeLa cells were cultured in 24-well cell culture plates as confluent monolayers. After 24 h, medium was removed and cells were overlaid with serial ten-fold dilutions of supernatant harvested from virus-infected cell lines or from homogenized mouse organs after 3 freeze/thaw cycles. Cells were then incubated at 37° C. for 30 min and, after removal of the supernatant, overlaid with agar containing Eagle's minimal essential medium (MEM). Three days later, the cells were stained with 0.025% neutral red in phosphate-buffered saline (PBS). Virus titers were determined by plaque counting 3 h after staining.

Cell Killing Assay

Colorectal carcinoma cells were seeded in 96-well plates and, on the following day, when cells reached complete confluence, the medium was carefully removed and virus solution (100 µl) was added at multiplicity of infection (MOI) of 1, 10 and 100. After 30 min incubation at 37° C. and 5% CO2, virus-containing medium was removed and fresh medium was added and cells incubated for different periods. To fix the cells, the medium was removed, the cells were washed with PBS and 10% trichloroacetic acid (TCA) (Carl Roth, Karlsruhe, Germany) was added. Following an incubation of 10 min, TCA was removed and 30 µl crystal violet solution (Carl Roth, Karlsruhe, Germany) was added. After 5 min incubation, wells were washed with PBS several times, the plate was allowed to dry overnight and photographed.

CVB3 RNA Quantification

Colorectal carcinoma cells were seeded in 96 well plates and infected with CVB3 strains. Twenty-four hours later plates were subjected to three freeze/thaw cycles and the collected supernatant centrifuged for 20 min at 2,000×g and 4° C. to remove cellular debris. Viral RNA was isolated from the supernatant with High Pure viral nucleic acid kit (Roche, Mannheim, Germany) according to the manufacturer's instructions, followed by DNase I digestion (Peqlab, Erlangen, Germany). The viral RNA was reverse transcribed using the High-Capacity cDNA reverse transcription kit (Applied Biosystems Inc., Foster City, Calif., USA). For quantification of viral RNA, real-time PCR was performed using CFX96 Real-Time System combined with a C1000 Thermal Cycler (Bio-Rad), using the forward primer, 5'-CCCTGAATGCGGCTAATCC (SEQ ID NO:3) and the reverse primer 5'-ATTGTCACCATAAGCAGCCA (SEQ ID NO:4) in Sso Fast™ EvaGreen Supermix (Bio-Rad). Cycle times were as follows: one cycle at 50° C. for 2 min followed by 94° C. for 10 min, 40 cycles at 94° C. for 15 s, and 60° C. for 60 s. A standard curve was used to calculate the number of CVB3 genome copies. The standard curve was prepared using 10-fold serial dilutions of 146 bp PCR fragment of CVB3 plasmid, which was amplified with the forward and reverse primers mentioned above.

Flow Cytometric Analysis of CAR and DAF Expression

Colorectal carcinoma cells were washed with PBS and detached from cell culture plates using PBS-2 mM EDTA solution. After washing with PBS the cells were stained on ice with monoclonal mouse anti-CAR/IgG1 (clone RmcB) antibody (Merck KGaA, Darmstadt, Germany) or with monoclonal mouse anti-DAF/CD55 (Merck) for 1 h at a dilution of 1:200. Cells were washed again with PBS and resuspended in Alexa Fluor 488-conjugated donkey anti-mouse IgG antibody (Life Technologies GmbH, Darmstadt, Germany), which was diluted 1:400 in PBS, and incubated for 45 min. After a further wash step with PBS, the cells were resuspended in PBS+1% formaldehyde and analyzed by flow cytometry using a MACSQuant® Flow Cytometers (Miltenyi Biotec GmbH, Bergisch Gladbach, Germany) and FlowJo, Data Analysis Software (Tree Star, San Carlos, Calif., USA). The mean fluorescence intensity was calculated by determining the geometric mean of CAR or DAF-expressing cells minus the geometric mean of a negative control sample.

In Situ Hybridization

Probes for the detection of CVB3 RNA by in situ hybridization were generated using the Dig RNA labeling Kit (Roche, Mannheim, Germany) using the pCVB3-R1 plasmid, which was linearized with SmaI as previously described (28). Pretreatment, hybridization and washing steps were done as described previously (29). Detection of the DIG-labeled RNA-probe was performed with a horseradish peroxidase-conjugated anti-Digoxigenin antibody (Roche, 1:100) and HistoGreen (Linaris GmbH, Dossenheim, Germany) as substrate. Sections were counterstained with hematoxilin and mounted with Pertex mounting media (Medite, Burgdorf, Germany).

In Vivo Experiments

Animal experiments were performed in accordance with the principles of laboratory animal care and all German laws regarding animal protection. DLD1 cells ($5 \times 10^6$ cells) were inoculated subcutaneously into the right and left flanks of 6 weeks old BALB/c nude mice. Tumor burdens were measured daily by hand caliper and CVB3 strains was injected intratumorally at a dose of $3 \times 10^6$ plaque forming units (PFU) per animal into one of the tumors when the tumor size reached 0.4-0.5 cm.

Histopathological Analysis

The mouse tissues and explanted human tumors were fixed in 4% paraformaldehyde, embedded in paraffin, and 5 µm thick tissue sections were cut and stained with hematoxylin and eosin (H&E) to visualize and quantify cell destruction and inflammation.

Statistical Analysis

Statistical analysis performed with GraphPad Prism 5.03 (GraphPad Software, Inc., La Jolla, Calif., USA). Results are shown as mean±SEM for each group. Statistical significance was determined by use of the two-tailed unpaired Student t test for cell culture investigations and by use of the one-tailed Mann-Whitney U-test for in vivo investigations. Differences were considered significant at $P<0.05$. Survival curves were plotted according to Kaplan-Meier method (log-rank-test).

Example 1: Functionality and Construction of CVB3 PD

The Appplicant received the starting virus PD from Michaela Schmidtke, (Institute of Virology and Antiviral Therapy, University of Jena), which sequence has been published (GenBank ID: AF231765.1; ncbi.nlm.nih.gov/nuccore/AF231765). The virus replicates in CAR/DAF-negative CHO cells and can be propagated in them. The virus was partially sequenced after multiplication.

A comparison of the PD variant used herein and the state of the art sequence of PD was performed. There, it was shown that the inventive PD variant used herein has in the VP3 protein a mutation towards the PD variant described in the literature (FIG. 2B), which is why it was designated as PD-0 in the following. In more detail, on nucleic acid level there are in total 5 nucleotide differences towards the virus PD reported in literature (FIG. 2A). One of them in 5'UTR and the others in VP1 (one) and VP3 (three). Among the nucleotide differences is one silent mutation in VP1 and another silent mutation in VP3, which have no effect on amino acid sequence. The other two are in VP3 region, and made differences in two amino acids compared to the state of the art PD sequence. The first amino acid change is at VP3 34 aa, i.e., position 366 in SEQ ID NO:2 (FIG. 2B). According to the state of PD sequence in bank, which was uploaded by Schmitdke et al., the amino acid at said position is "T", whereas per the inventors of the present invention, sequences in PD-0 show a "M" at that position. The last amino acid change is at VP3 237aa, i.e., position 569 in SEQ ID NO:2 (FIG. 2B). According to the state of the art PD sequence in GenBank, which was uploaded by Schmitdke et al., the amino acid at said position is "F", whereas per the inventors of the present invention, sequences in PD-0 show a "Y" there. Whether these single mutations are responsible for all the changes in the functions of PD-0 versus the parental PD is not known. In any case, the inventors could show that the inventive PD-0 variant can multiply in different target cells and destroy them by cell lysis (FIG. 5). New viruses are released which, in turn, infect and destroy further cells. At the same time, it is—at the best knowledge of the inventors—assumed that the virus-induced immune mechanisms contribute to the enhancement of tumor cell lysis.

Example 2: CAR and DAF are Differentially Expressed on Colorectal Carcinoma Cell Lines Recently, it has been shown that the CVB3 strains Nancy, 31-1-93 and H3 use CAR and DAF for infection, whereas the strain PD uses sulfated Heparan (HS), but may also bind to CAR and DAF. We focused on colorectal cancer as this is one of the most common cancers worldwide with poor outcome and different colorectal cancer cell lines do express HS6ST2, the enzyme, which catalyses the transfer of sulfate groups to position 6 of the N-sulfoglucosamine residue in HS.

Figure 3A:
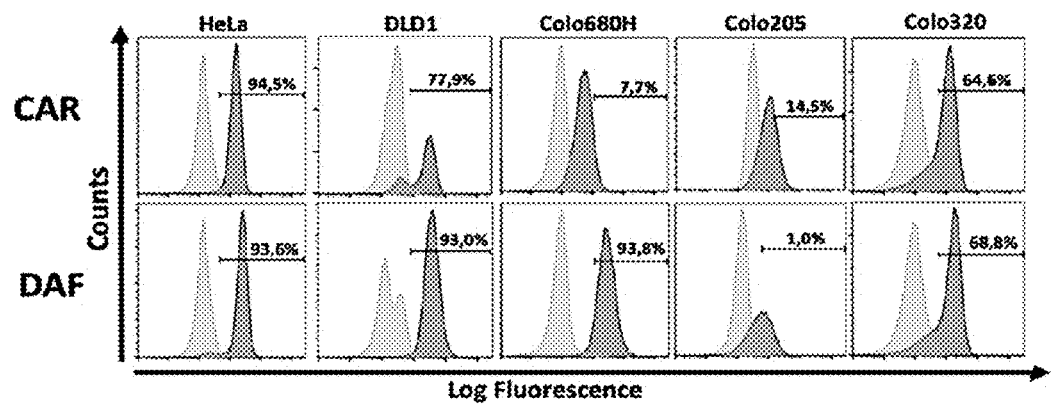
Figure 3A:
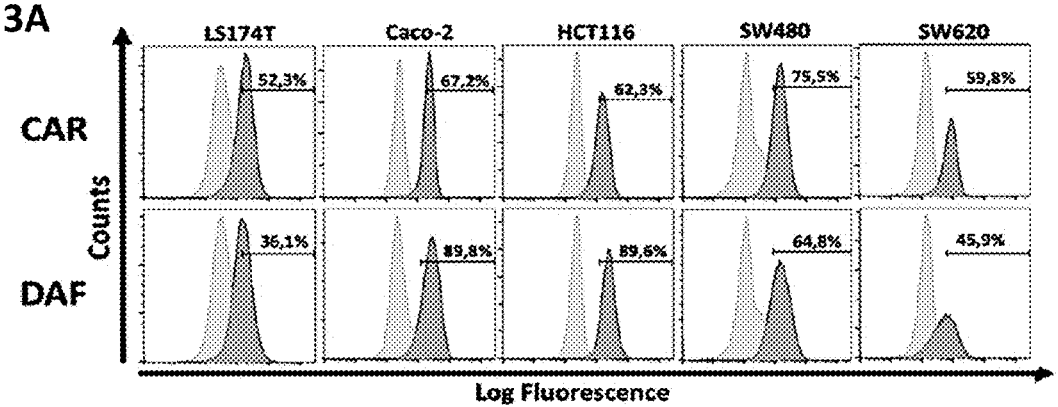
Figure 3B:
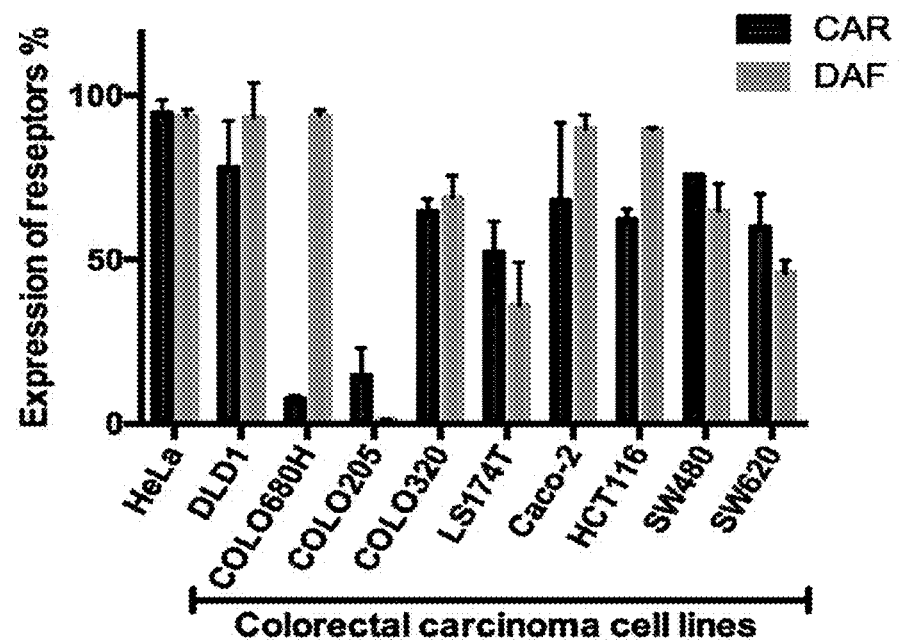

Expression of virus receptors on the cell surface is an important prerequisite for virus infection. CAR and DAF represent the primary and the co-receptor for CVB3, respectively. To determine the expression of the different CVB3 receptors on colorectal carcinoma cells, we measured the level of CAR and DAF of nine colorectal carcinoma cell lines (Colo680h, Colo205, DLD1, Colo320, Caco-2, HCT116, SW480, SW620, LS174T) using flow cytometry. Seven cell lines express moderate levels of CAR, while two cell lines (Colo680H and Colo205) express CAR only at a low level. Four cell lines showed high (Colo680, DLD1, Caco2, HCT116) and moderate (Colo320, SW480, SW620, LS174T) levels of DAF expression, whereas one cell line (Colo205) almost completely lacks DAF on the cell surface (FIGS. 3A, and 3B). These data demonstrate that CAR and DAF are expressed at variable levels on the cell surface of colorectal carcinoma cell lines, with the majority of cell lines expressing CAR and DAF at high or moderate levels.

Example 3: CVB3 Strains Differentially Infect and Lyse Colorectal Carcinoma Cell Lines To determine whether CAR/DAF expression may influence the ability of CVB3 Nancy, 31-1-93, H3 and PD-0 to infect and lyse colorectal carcinoma cell lines, we used five human colorectal carcinoma cell lines (DLD1, Colo680h, Colo205, Colo320 and LS174T) exhibiting different levels of CAR and DAF expression. These cell lines were infected with a virus strain at an MOI of 1 or 10, and viral infection was determined by measurement of the amount of viral RNA genomes 24 h after infection by quantitative RT-PCR. Each virus strain was detected in its target cell line, but there were significant differences in the infection rates. High and moderate infection rates were detected for PD-0 in all cell lines. Strain 31-1-93 showed also moderate and high infection rates, but only in some of the colorectal carcinoma cell lines (LS174T and DLD1). In the other cell lines, it was low. The infection rates for Nancy and H3 were generally low (data not shown).

Figure 4:
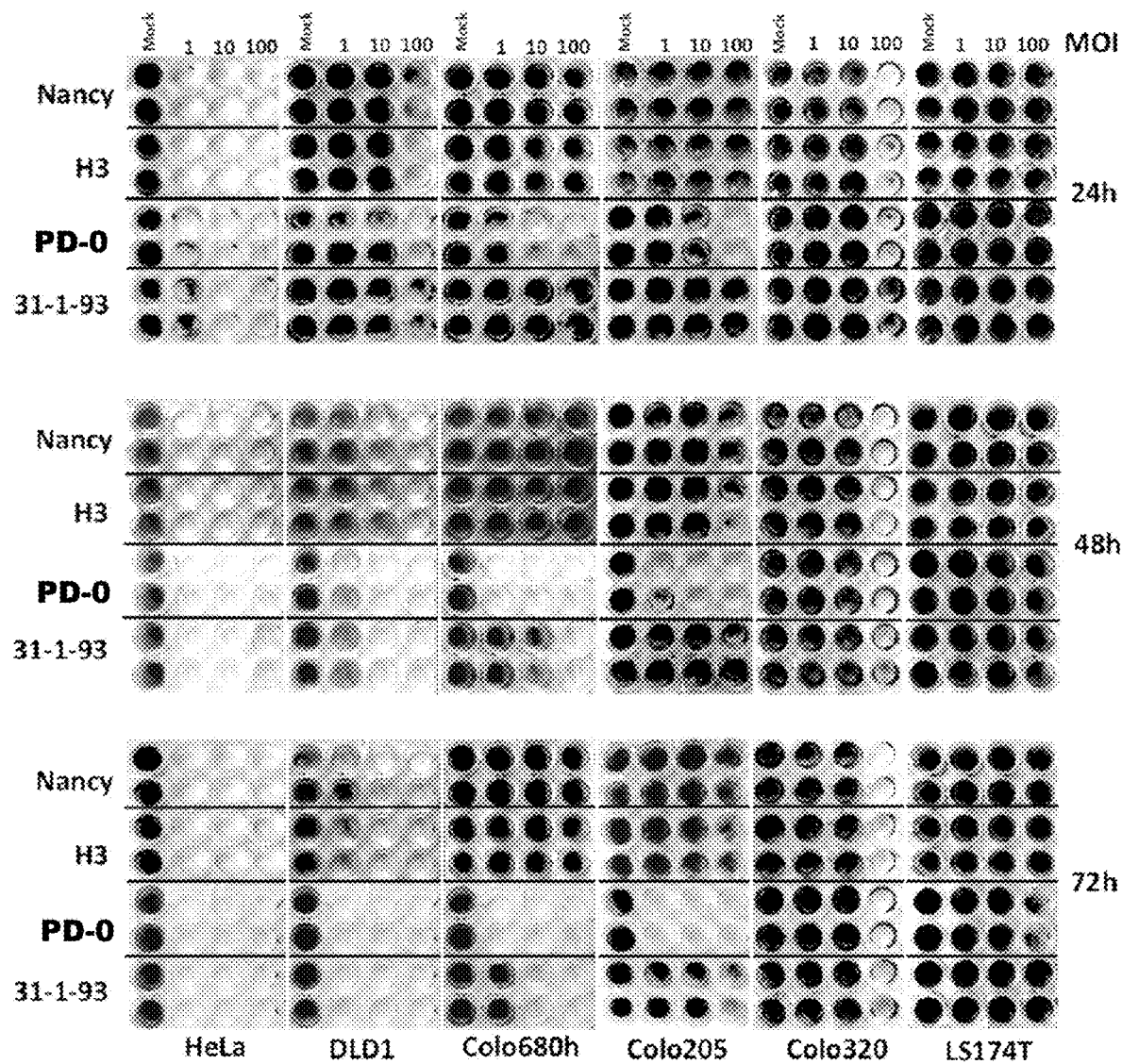

To determine cytolytic activity of the CVB3 strains, colorectal carcinoma cell lines were infected with the viruses at an MOI of 1, 10 or 100, and analyzed 24 h, 48 h and 72 h for cytotoxicity using crystal violet staining. The cytolytic efficiency of the CVB3 strains was highly variable. Much like the infection data, PD-0 showed strong cytolytic activity in DLD1, Colo680H and Colo205 and moderate activity in Colo320 and LS174T. The strain 31-1-93 induced cell lysis in four of the five investigated cell lines, but high cytolytic activity was only detected in the cell line DLD1. Nancy and H3 had comparatively low cytolytic activity. Cytolysis was only observed at high MOIs in DLD1 and Colo320 cells. (FIG. 4, and Table 1). Thus, there was no clear correlation between CAR/DAF expression levels and infection/lysis of colorectal carcinoma cell lines by the CVB3 strains. These data demonstrate that the inventive CVB3 strain PD-0 most efficiently infected and lysed each of the colorectal carcinoma cell lines. It is important to mention that the DLD1 cell line tested here is highly resistant to radiation and against 5-fluorouracil, which is used as chemotherapeutic agent for the treatment of colorectal cancer. Unlike the other CVB3 strains, PD-0 has only low affinity to CAR, but can use N- and 6-O-sulfated HS as receptor to enter cells. The specific receptor tropism to HS therefore seems to be—without being bound by this theory—the most probable explanation for the high infection and lytic capacity of inventive PD-0 in the colorectal carcinoma cell lines. CVB3 viruses according to the present invention may therefore and for said additional features presented be an alternative treatment modality for colorectal cancers, which are resistant to conventional therapies.

TABLE 1

CAR and DAF expression and lytic activity of CVB3 strains in different colorectal carcinoma cell lines.

| Colorectal Carcinoma Cell Lines | Average Expression [%] | | Sensitivity of Cell Lines Against CVB3 Variants | | | |
|---|---|---|---|---|---|---|
| | CAR | DAF | Nancy | H3 | 31-1-93 | PD-0 |
| DLD 1 | 77.9 ± 14.3 | 93.0 ± 10.8 | ++ | ++ | ++++ | +++++ |
| Colo680H | 7.7 ± 0.9 | 93.8 ± 1.6 | | | ++ | +++ |
| Colo205 | 14.5 ± 8.6 | 1.0 ± 0.1 | | + | + | +++++ |
| Colo320 | 64.6 ± 3.8 | 68.8 ± 6.7 | + | + | + | + |
| LS174T | 52.3 ± 9.3 | 36.1 ± 13.1 | | | | + |

Sensitivity was indicated relatively by the number of "+".
"+++++" = complete lysis (100%),
"++++" = 80% lysed, etc. A free field means resistance of the cell line to the virus variant.

Example 4: CVB3 Strains have Strong Oncolytic Activity In Vivo

Figure 5A:
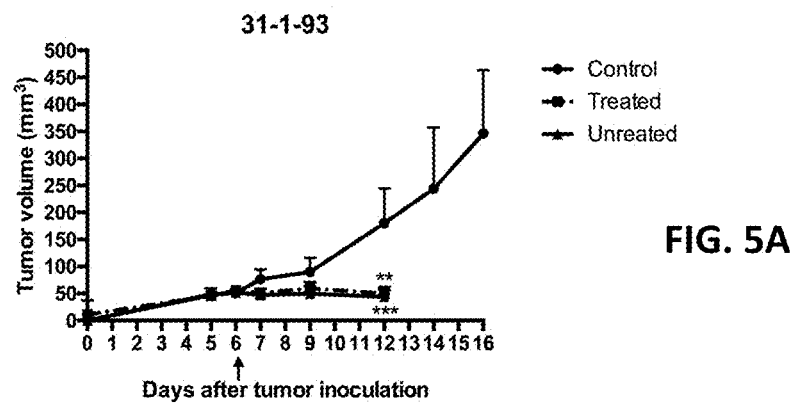
Figure 5B:
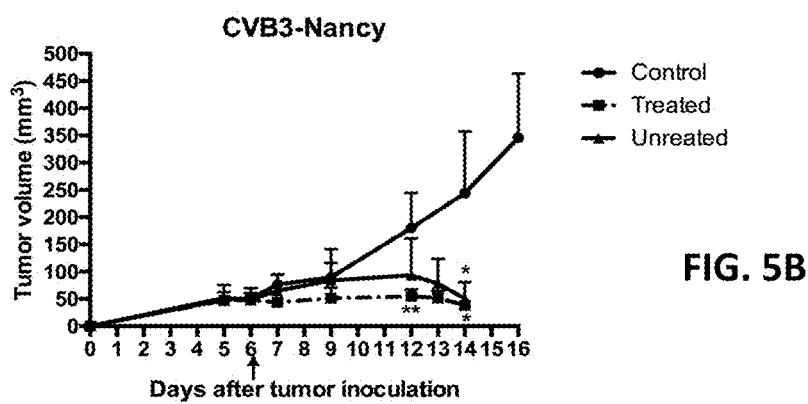
Figure 5C:
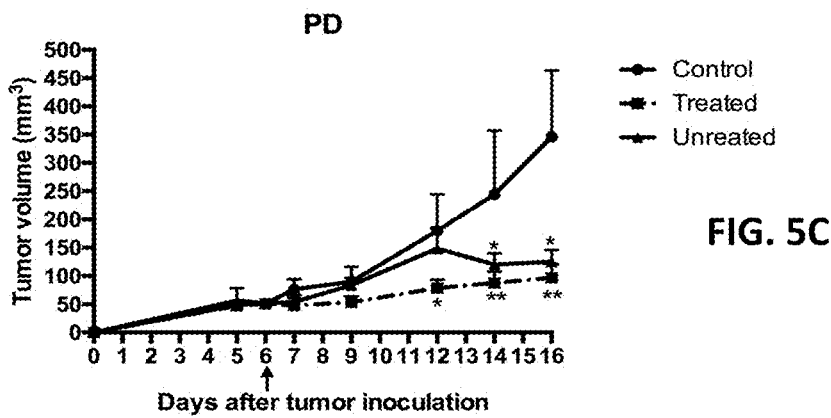
Figure 6A:
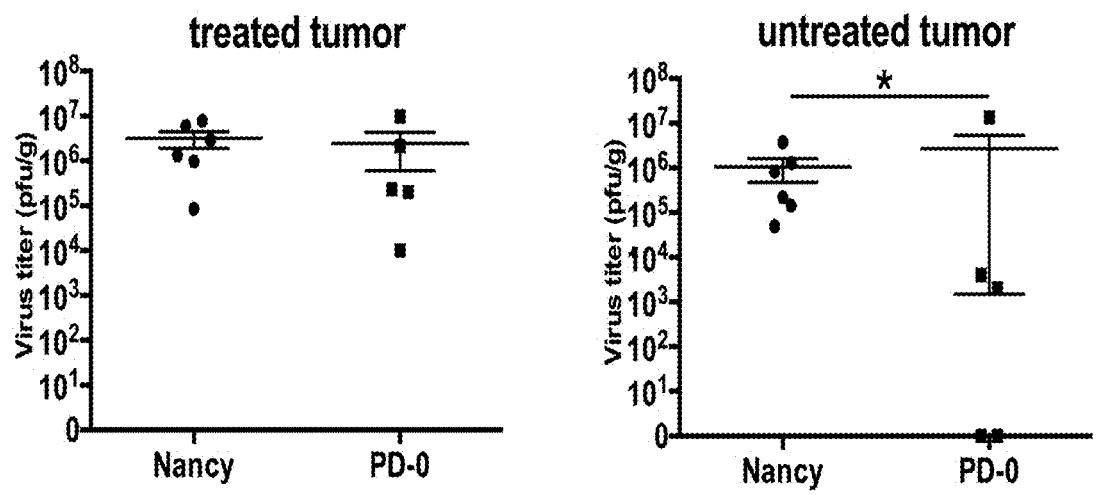
Figure 6B:
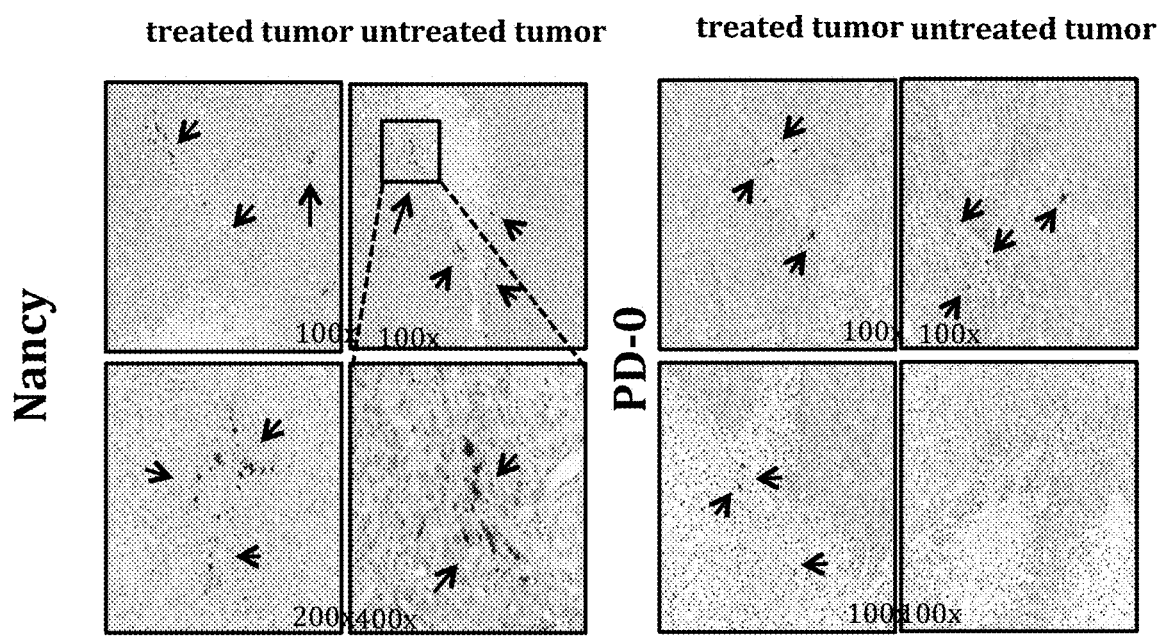

To evaluate oncolytic efficiency of CVB3 strains in vivo, a xenograft BALB/c mouse tumor model was established with the DLD1 human colorectal carcinoma cell line. Tumor cells were inoculated bilaterally into the flanks of the animals and only one of the two tumors was injected with single dose of 3×10$^6$ PFU of CVB3 Nancy, 31-1-93, or PD-0. Treatment with any of the three viruses resulted in significant suppression of tumor growth of both the virus-injected tumor and the contralateral untreated tumor when compared with uninfected mice tumors (P<0.05; FIGS. 5A-5C). Measurement of the amount of infectious virus in the tumors of Nancy and PD-O-infected animals by plaque assay 8 and 10 days after virus injection, respectively, showed that both viruses were detected at similar levels (between 3.2 and 7.2×10$^6$ PFU/g) in the primary injected tumor. Both viruses were also detected in the contralateral, untreated tumor, but the amount was significantly lower in the PD-0 injected group than in Nancy treated animals (P<0.05; FIG. 6A). Moreover, in two of five investigated animals, PD-0 was not detected in the untreated tumor. In situ hybridization confirmed the presence of viral genomic RNA in the tumors of Nancy and PD-0 infected animals, as well as the absence of virus in untreated tumors of two PD-0 infected animals, which also were negative when measured for replicating virus. The inventors also showed that viruses were located in mononuclear immune cells, probably macrophages, within the tumor mass or on the border between the tumor stroma and tumor cells (FIG. 6B). Taken together, these results demonstrate that CVB3 Nancy, 31-1-93, and PD-0 have strong oncolytic activity in vivo and this activity is not only restricted to injected tumor but also is seen in non-injected, distant tumors. Whereas these results demonstrate per se the efficacy of CVB3-mediated oncovirotherapy in colorectal cancer, suppression of the untreated tumor reveals the potential of the CVB3-strains to treat metastatic or disseminated colorectal cancer.

Figure 7:
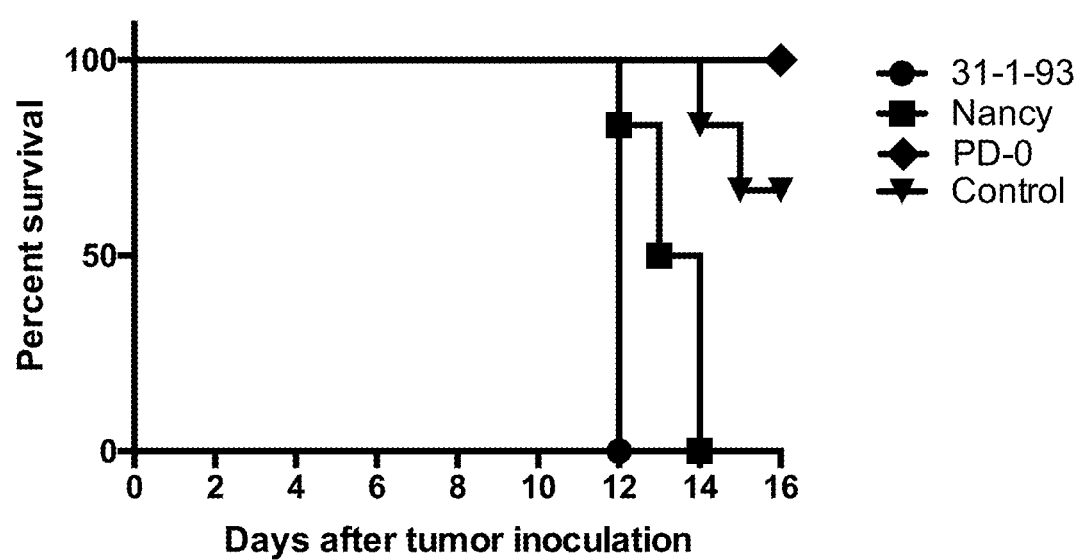

Example 5: CVB3 Nancy and 31-1-93, but not PD-0, Induce Severe Side Effects in Treated Mice Intratumoral injection of CVB3 Nancy and 31-1-93 resulted in severe side effects. All animals, which were injected with 31-1-93, died six days after intratumoral virus injection and animals treated with Nancy were moribund six (one animal), seven (one animal) and eight days (four animals) after virus administration and were sacrificed. In contrast, the animals treated with PD-0 were alive 10 days after intratumoral virus injection (FIG. 7).

Figure 8A:
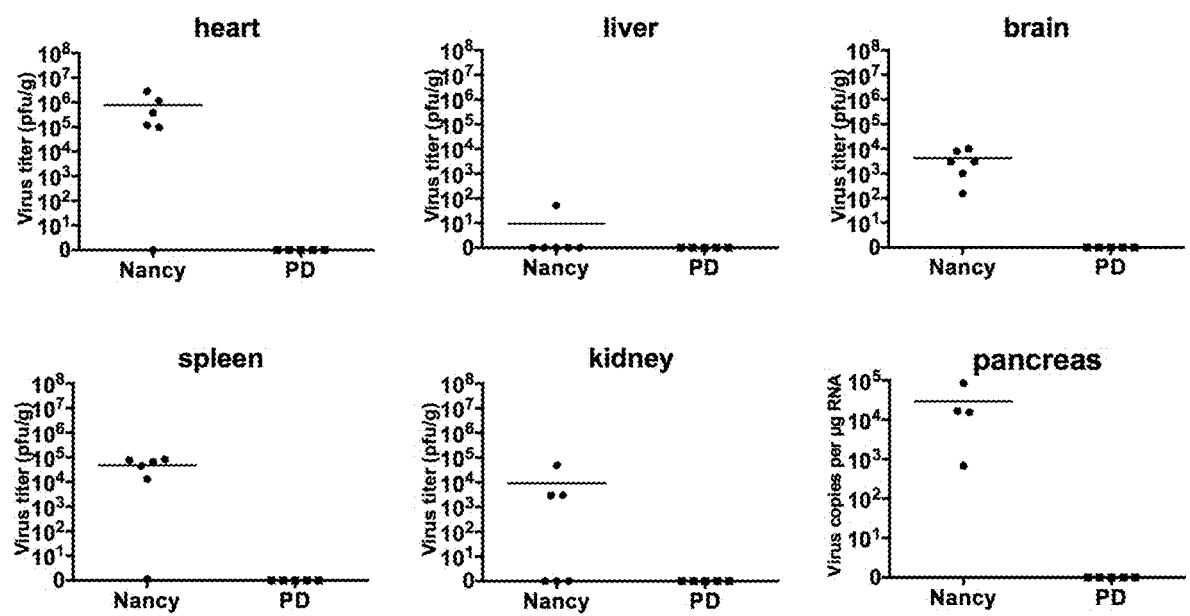
FIGS. 8A and 8B. Viral load and pathological alterations of CVB3 Nancy and PD-0 in organs of tumor bearing mice. Organs of the animals were harvested at the time points when animals were sacrificed as described under FIG. 5.
Figure 8B:
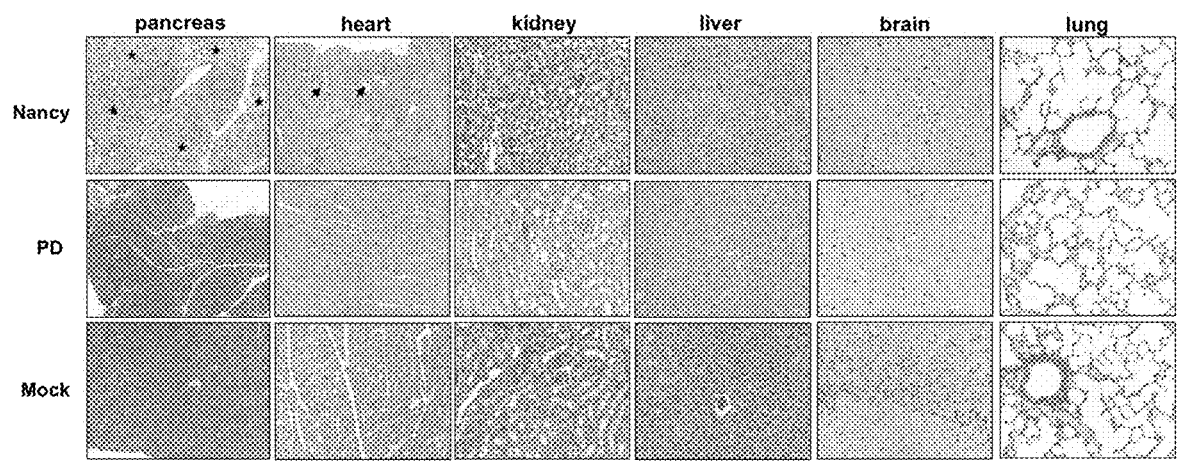

To elucidate the cause of the severe side effects in the Nancy strain, we investigated occurrence of Nancy and PD-0 infection in heart, liver, brain, spleen, kidney and pancreas, respectively. Using plaque assays to detect replicating virus. The highest virus titers, of about $10^6$ PFU/g, were measured in the heart of the Nancy treated group (FIG. 8A). CVB3 Nancy was also detected in the spleen, kidney and brain, but at distinctly lower levels, whereas it could only sporadically be detected in the liver (one of six animals) at a very low titer ($10^2$ PFU/g). The pancreas is the most susceptible organ for CVB3 in mice (Pinkert et al., 2009). Examination of the pancreas tissue in Nancy infected animals during dissection showed reduced organ size (not shown) indicating major damage to the tissue. As the destruction of the pancreas by CVB3 virus made the tissue unsuitable for determination of infectious virus by plaque assay, we carried out real-time RT-PCR to quantify the virus genomes. High amounts ($10^3$ to $10^5$ copies per µg RNA) of Nancy viral RNA were detected in the pancreas (FIG. 8A). In sharp contrast, no infectious virus was recovered from any organ of the five PD-0 treated animals. Histological examination of mouse tissues (pancreas, heart, kidney, liver, brain and lung) confirmed different toxic activity of Nancy and PD-0. The exocrine pancreas of Nancy infected animals was nearly completely destroyed and heart tissue of these animals showed distinct inflammation. All other organs of Nancy infected animals were unaffected. In contrast, all organs of the five PD-0 treated animals did not show any alterations (FIG. 8B). Interestingly, the inventors could show the presence of CVB3 Nancy and CVB3 PD-0 RNA in immune cells within the tumor masses and on the tumor-stroma border zone, whereas tumor cells seemed not to be infected.

Thus, most importantly said animals treated with CVB3 strain PD-0 did not show any virus-induced side effects. No systemic infection with CVB3 PD-0 was detected and virus could not be recovered from the organs of these animals. In addition, PD-0 is nonpathogenic in immune-competent mice. In sharp contrast, two other analyzed CVB3 strains, Nancy and 31-1-93, although showing similar anti-tumor efficiency as PD-0, induced severe systemic infection in mice, leading to the death of the animals. Therefore, these findings reveal PD-0 as an efficient and safe CVB3 strain for treatment of colorectal cancer and a promising candidate for the treatment of cancer, particularly cancer comprising cancer cells which expose and express heparin sulfate receptors.

REFERENCES

Fukuhara H, Ino Y, Todo T. Oncolytic virus therapy: A new era of cancer treatment at dawn. Cancer Sci 2016; 107:1373-9.

Kaufman H L, Kohlhapp F J, Zloza A. Oncolytic viruses: A new class of immunotherapy drugs. Nature reviews. Drug discovery. 2015; 14:642-662.

Berry L J, Au G G, Barry R D, Shafren D R. Potent oncolytic activity of human enteroviruses against human prostate cancer. Prostate 2008; 68:577-87.

Shafren D R, Au G G, Nguyen T, Newcombe N G, Haley E S, Beagley L, et al. Systemic therapy of malignant human melanoma tumors by a common cold-producing enterovirus, coxsackievirus a21. Clin Can Res 2004; 10:53-60.

Skelding K A, Barry R D, Shafren D R. Systemic targeting of metastatic human breast tumor xenografts by Coxsackievirus A21. Breast Cancer Res Treat 2009; 113:21-30.

Miyamoto S, Inoue H, Nakamura T, Yamada M, Sakamoto C, Urata Y, Okazaki T, Marumoto T, Takahashi A, Takayama K, Nakanishi Y, Shimizu H, Tani K. Coxsackievirus b3 is an oncolytic virus with immunostimulatory properties that is active against lung adenocarcinoma. Cancer research. 2012; 72:2609-2621.

Bergelson J M, Krithivas A, Celi L, Droguett G, Horwitz M S, Wickham T, et al. The murine CAR homolog is a receptor for coxsackie B viruses and adenoviruses. J Virol 1998; 72:415-9.

Bergelson J M, Mohanty J G, Crowell R L, St John N F, Lublin D M, Finberg R W. Coxsackievirus B3 adapted to growth in R D cells binds to decay-accelerating factor (CD55). J Virol 1995; 69:1903-6.

Fechner H, Wang X, Wang H, Jansen A, Pauschinger M, Scherubl H, Bergelson J M, Schultheiss H P, Poller W. Trans-complementation of vector replication versus coxsackieadenovirus-receptor overexpression to improve transgene expression in poorly permissive cancer cells. Gene Ther. 2000; 7:1954-1968.

Stein E A, Pinkett S, Becher P M, Geisler A, Zeichhardt H, Klopfieisch R, Poller W, Tschope C, Lassner D, Fechner H, Kurreck J. Combination of rna interference and virus receptor trap exerts additive antiviral activity in coxsackievirus b3-induced myocarditis in mice. J Infect Dis. 2015; 211:613-622.

Pinkert S, Westermann D, Wang X, Klingel K, Dorner A, Savvatis K, Grossl T, Krohn S, Tschope C, Zeichhardt H, Kotsch K, Weitmann K, Hoffmann W, Schultheiss H P, Spiller O B, Poller W, Fechner H. Prevention of cardiac dysfunction in acute coxsackievirus b3 cardiomyopathy by inducible expression of a soluble coxsackievirus-adenovirus receptor. Circulation. 2009; 120:2358-2366.

Andreoletti L, Leveque N, Boulagnon C, Brasselet C, Fornes P. Viral causes of human myocarditis. Archives of cardiovascular diseases. 2009; 102:559-568.

Andreoletti L, Venteo L, Douche-Aourik F, Canas F, Lorin de la Grandmaison G, Jacques J, Moret H, Jovenin N, Mosnier J F, Matta M, Duband S, Pluot M, Pozzetto B, Bourlet T. Active coxsackieviral b infection is associated with disruption of dystrophin in endomyocardial tissue of patients who died suddenly of acute myocardial infarction. J. Am. Col I. Cardiol. 2007; 50:2207-2214.

Ronellenfitsch S, Tabatabai J, Bottcher S, Diedrich S, Frommhold D, Schubert-Bast S, Poeschl J, Schnitzler P. First report of a chinese strain of coxsackie b3 virus infection in a newborn in Germany in 2011: A case report. Journal of medical case reports. 2014; 8:164.

Schmidtke M, Merkle I, Klingel K, Hammerschmidt E, Zautner A E, Wutzler P. The viral genetic background determines the outcome of coxsackievirus B3 infection in outbred NMRI mice. J Med Virol 2007; 79:1334-42.

While the present invention has been particularly shown and described with reference to the structures, compositions and methods disclosed herein and as illustrated in the drawings, it is not confined to the details set forth and this invention is intended to cover any modifications and changes as may come within the scope and spirit of the following claims. All publications and patent literature described herein are incorporated by reference in entirety to the extent permitted by applicable laws and regulations.

Sequence listings and related materials in the ASCII text file named "FGP_Corrected-Seq_ST25.txt" and created on Mar. 12, 2018 with a size of about 12 kilobytes, is hereby incorporated by reference.

The invention claimed is:

1. A method for treating cancer in a subject in need thereof, comprising administering to said subject a therapeutically effective amount of a PD variant of the Coxsackie B3 group (CVB3) virus, wherein the PD variant is defined by an amino acid sequence comprising SEQ ID NO:2, and wherein the cancer is selected from the group consisting of colorectal carcinoma, esophageal cancer, breast cancer, lung cancer, pancreatic cancer, prostate cancer, gastric cancer and liver cancer.

2. The method according to claim 1, wherein the PD variant of the CVB3 virus is defined by a nucleotide sequence comprising SEQ ID NO:1.

3. The method according to claim 1, wherein the range of the therapeutically effective amount of the PD variant of the CVB3 virus is between about $5 \times 10^5$ to about $3 \times 10^8$ plaque forming units (PFU).

4. The method according to claim 1, wherein the cancer is colorectal carcinoma.

5. The method according to claim 1, wherein the cancer is in cells that express on their surface a receptor for the CVB3 PD variant, said receptor comprising a N- and/or a 6-O-sulfated heparan.

6. A pharmacological composition, comprising:
   i) a therapeutically effective amount of a PD variant of the Coxsackie B3 group (CVB3) virus, wherein the PD variant is defined by an amino acid sequence comprising SEQ ID NO:2; and
   ii) at least one pharmaceutically acceptable excipient, diluent or carrier.

7. The composition according to claim 6, wherein the PD variant of the CVB3 virus is defined by a nucleotide sequence comprising SEQ ID NO:1.

8. The composition according to claim 6, wherein the pharmacological composition is used for treating cancer where the cancer cells express on their surface a receptor for the CVB3 PD variant, said receptor comprising a N- and/or a 6-O-sulfated heparan.

9. A method for treating cancer in a subject in need thereof, said method comprising the steps of:
   (i) confirming expression of heparin sulfate (HS) on the surface of a target population of cancer cells in a subject; and
   (ii) administering to said subject a therapeutically effective amount of a PD variant of the Coxsackie B3 group (CVB3) virus to infect said target population of cancer cells via binding to at least said HS, causing infected cancer cells to undergo viral lysis, wherein the CVB3 PD variant is defined by an amino acid sequence comprising SEQ ID NO:2.

10. The method according to claim 9, wherein the CVB3 PD variant is further defined by a nucleotide sequence comprising SEQ ID NO:1.

11. The method according to claim 9, wherein the cancer is selected from the group consisting of colorectal carcinoma, esophageal cancer, breast cancer, lung cancer, pancreatic cancer, prostate cancer, gastric cancer and liver cancer.

12. The method according to claim 9, wherein step (i) comprises using an antibody against a heparan sulfate or a sulfotransferase.

13. The composition according to claim 6, wherein the range of the therapeutically effective amount of the PD variant of the CVB3 virus is between about $5 \times 10^5$ to about $3 \times 10^8$ plaque forming units (PFU).

* * * * *